US011000655B1

(12) United States Patent
Fox et al.

(10) Patent No.: US 11,000,655 B1
(45) Date of Patent: May 11, 2021

(54) DEVICES, SYSTEMS, AND METHODS FOR PROTECTING HEALTHCARE WORKERS FROM AIRBORNE PATHOGENS

(71) Applicant: INQUIS MEDICAL, INC., Atherton, CA (US)

(72) Inventors: William Jason Fox, San Mateo, CA (US); William L. Gould, Santa Fe, NM (US); Matthew Allison Herron, Hayward, CA (US); Andrew Ivan Poutiatine, Mill Valley, CA (US); Mojgan Saadat, Atherton, CA (US); Vahid Saadat, Atherton, CA (US)

(73) Assignee: INQUIS MEDICAL, INC., Atherton, CA (US)

( * ) Notice: Subject to any disclaimer, the term of this patent is extended or adjusted under 35 U.S.C. 154(b) by 0 days.

(21) Appl. No.: 16/882,413

(22) Filed: May 22, 2020

Related U.S. Application Data

(60) Provisional application No. 63/015,429, filed on Apr. 24, 2020, provisional application No. 63/019,986, (Continued)

(51) Int. Cl.
*A61M 16/00* (2006.01)
*A61M 16/10* (2006.01)
*A61M 16/06* (2006.01)

(52) U.S. Cl.
CPC ...... *A61M 16/009* (2013.01); *A61M 16/0616* (2014.02); *A61M 16/1065* (2014.02);
(Continued)

(58) Field of Classification Search
CPC ............ A61M 16/009; A61M 16/1065; A61M 16/0616; A61M 2206/11;
(Continued)

(56) References Cited

U.S. PATENT DOCUMENTS 3,822,698 A   7/1974 Guy
4,320,754 A * 3/1982 Watson ................. A61M 16/08
                                                                128/204.25
(Continued)

FOREIGN PATENT DOCUMENTS

WO   WO2016/122435 A1   8/2016
WO   WO2016/210192 A1   12/2016
WO   WO2018/140841 A1   8/2018

OTHER PUBLICATIONS

Khoury et al.; Aerosolized particle reduction—a novel cadaveric model and a negative airway-pressure respirator (NAPR) system to protect healthcare workers from COVID-19; Otolaryngology—Head and Neck Surgery; doi:10.1177/0194599820929275; 5 pages; May 19, 2020.

(Continued)

*Primary Examiner* — Victoria Murphy
(74) *Attorney, Agent, or Firm* — Shay Glenn LLP

(57) ABSTRACT

A method of removing exhaled material from a medical procedure field adjacent to a subject's nose and mouth. In some embodiments the method includes the steps of placing an isolation barrier at least partially surrounding the subject's nose and mouth to define the medical procedure field; controlling air flow into the medical procedure field with the isolation barrier; and evacuating air from the medical procedure field at an air evacuation rate greater than or equal to the subject's respiratory minute volume. The invention also provides a system for creating an isolated medical procedure field around a subject's nose and mouth.

38 Claims, 25 Drawing Sheets

Related U.S. Application Data filed on May 4, 2020, provisional application No. 63/021,033, filed on May 6, 2020.

(52) U.S. Cl.
CPC . *A61M 2206/11* (2013.01); *A61M 2210/0618* (2013.01); *A61M 2210/0625* (2013.01)

(58) Field of Classification Search
CPC .. A61M 2210/0618; A61M 2210/0625; A61B 1/018; A61B 90/40; A41D 13/11; A62B 18/08

See application file for complete search history.

(56) References Cited

U.S. PATENT DOCUMENTS

| | | | |
|---|---|---|---|
| 5,427,091 A | | 6/1995 | Phillips |
| 5,431,158 A | * | 7/1995 | Tirotta .............. A61M 16/0488 128/200.26 |
| 5,694,927 A | | 12/1997 | Bohmfalk |
| 5,803,076 A | | 9/1998 | Myers |
| 6,257,236 B1 | | 7/2001 | Dutkiewicz |
| 7,479,103 B2 | | 1/2009 | Ellen |
| 7,503,890 B2 | | 3/2009 | Kubicsko et al. |
| 8,365,734 B1 | | 2/2013 | Lehman |
| 9,310,088 B2 | | 4/2016 | Melikov et al. |
| 10,493,228 B2 | | 12/2019 | Reddy et al. |
| 2002/0162556 A1 | | 11/2002 | Smith et al. |
| 2003/0024533 A1 | * | 2/2003 | Sniadach .............. A61M 16/06 128/205.25 |
| 2005/0028811 A1 | | 2/2005 | Nelson et al. |
| 2005/0085686 A1 | | 4/2005 | Yeun et al. |
| 2006/0076013 A1 | * | 4/2006 | Berg ................... A61M 16/009 128/203.12 |
| 2008/0302365 A1 | * | 12/2008 | Cohen ............... A61M 16/0616 128/206.12 |
| 2009/0159083 A1 | | 6/2009 | Zettergren et al. |
| 2012/0240935 A1 | * | 9/2012 | Johansen .......... A61M 16/0045 128/205.17 |
| 2014/0083431 A1 | | 3/2014 | Burz et al. |
| 2014/0243600 A1 | | 8/2014 | Eisenberger |
| 2016/0022946 A1 | * | 1/2016 | Sislian ................... A61B 10/00 600/543 |
| 2017/0007795 A1 | * | 1/2017 | Pedro ................ A61M 16/0672 |
| 2020/0261320 A1 | * | 8/2020 | Rodriguez ............. B65D 33/14 |

OTHER PUBLICATIONS

The Pulse; New inventions help protect healthcare workers during covid-19 pandemic; 5 pages; retrieved from the interent (https://usupulse.blogspot.com/2020/05/new-invention-helps-protect-healthcare.html); on Jun. 15, 2020.

Workman et al.; Endonasal instrumentation and aerosolization risk in the era of COVID-19: simulation, literature review, and proposed mitigation strategies; InInternational forum of Allergy and Rhinology; https://doi.org/10.1002/air.22577; 22 pages. (Author Manuscript); Apr. 3, 2020.

* cited by examiner

DEVICES, SYSTEMS, AND METHODS FOR PROTECTING HEALTHCARE WORKERS FROM AIRBORNE PATHOGENS

CROSS REFERENCE TO RELATED APPLICATIONS

This application claims the benefit under 35 U.S.C. § 119 of U.S. Patent Appln. No. 63/015,429, filed Apr. 24, 2020; U.S. Patent Appln. No. 63/019,986, filed May 4, 2020; and U.S. Patent Appln. No. 63/021,033, filed May 6, 2020, the disclosure of each of which is incorporated by reference.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

This invention relates generally to the field of personal protection equipment (PPE) and more specifically to a new and useful system for protecting physicians and healthcare workers from airborne, aerosol-borne and particle-borne pathogens during medical examinations and medical procedures within or through the nose and/or mouth. Physicians and other health care professional performing procedures in and around a subject's airway (e.g., the nose, the mouth) can be exposed to air-borne pathogens carried by droplets and particles from the subject's exhaled breath, particularly if the subject sneezes or coughs. Some diagnostic and therapeutic procedures performed in and around the nose and mouth can increase the velocity of air in the subject's airway and thereby increase the creation and dissemination of droplets and particles in the subject's exhaled breath. Masks and respirators, such as an N95 respirator, can block such particles, but they can also block access to the nose and mouth, thereby preventing the performance of diagnostic and therapeutic procedures in the nose and mouth.

The outbreak of the COVID-19 pandemic, caused by the SARS-CoV-2 virus, has the world, and specifically healthcare workers and governing authorities, reevaluating personal protective equipment (PPE), and their associated guidelines for utilization, to slow the spread of the virus and to prepare for similar pandemics like this in the future. Pathogens, including the SARS-CoV-2 virus, the Ebola virus, bacterial, fungi, prions, micro-organisms and other pathogens are known to spread through the air by means of convective transport either alone (as in the case of fungal spores, for example) or attached to or entrapped by aerosols (such as those produced when a person sneezes or coughs, for example), airborne particles (such as dust, for example), or other transport media.

Since the emergence of the SARS-CoV-2 virus in late 2019, many authorities have mandated that everyone should cover their nose and mouth (with PPE such as with an N95 type respirator) to reduce transmission of air-borne pathogens. This use of PPE has been shown to help reduce the spread of the virus, however there are many instances where continuous coverage of the nose and mouth is impractical, such as medical procedures within the airway, procedures in the upper gastrointestinal (GI) tract, and/or dental exams, surgeries or procedures. In these examples, the person being examined (the subject) removes their mask, and healthcare workers and physicians get within inches of the subject's airway to treat or examine the subject.

It is well known in the medical and healthcare fields that normal human respiration can emit particulates, pathogens and/or aerosols from the nose and mouth. During normal breathing and talking these emitted particulates, pathogens and aerosols can travel significant distance, often measured in feet or tens of feet, from an individual. During episodic respiration events like coughing, sneezing, hiccupping, burping, clearing the throat, gasping or heavy breathing patterns, etc. these particulates, pathogens and/or aerosols may be more abundant and travel farther from a person. Furthermore, tissue manipulation and some medical interventions and procedures (such as abrasion type procedures) may cause these particulates, pathogens and/or aerosols to become more abundant and travel farther from the subject. Any of the above mentioned respiratory and medical events can result in a healthcare worker, medical staff, other subjects and other individuals to become exposed to an infectious agent or pathogen, and/or result in contamination of a room, equipment, furniture or other objects, even while wearing existing PPE.

Physicians from Stanford University reported on instances of infectious pathogens being spread to physicians and healthcare workers during endonasal endoscopic surgeries in their letter of precaution in the Journal of Neurosurgery. Based on the information presented in the letter, physicians started only performing only urgent/emergent surgeries and requiring the utilization of a powered air purifying respirator (PAPR) if endonasal surgery cannot be postponed in a COVID-19 positive subject. A powered air purifying respirator is a piece of personal protective equipment (PPE) that protects the individual healthcare worker wearing the piece of equipment by pulling air in, filtering the air and blowing the filtered air over the individual. This PPE has been shown to be effective, but the need to have this piece of equipment for every individual in the room makes this not a long term viable solution. Since this letter of caution was published, additional physicians have reported on continued investigations on the aerosolization of pathogens and particulates from a subject during various airway procedures. Physicians from the Massachusetts Eye and Ear Infirmary, the Harvard Medical School, and the Massachusetts General Hospital (all in Boston, Mass.) reported on the aerosolization risk during endonasal instrumentation.

Physicians in the above-mentioned report identified that aerosolization of particulates during endonasal procedures is a risk specifically due to sneezing as well as due to several common surgical procedures. They also noted that a use of a barrier significantly reduced the spread of the aerosols. "Endonasal Instrumentation and Aerosolization Risk in the Era of COVID-19: Simulation, Literature Review, and Proposed Mitigation Strategies" (reference: https://doi.org/10.1002/alr.22577) is incorporated in its entirety by reference.

The COVID-19 pandemic has brought awareness to the forefront that there remains an urgent need for the development of new devices, systems, and methods to prevent and manage the release of subject-generated air-borne pathogens, particulates, and aerosols in medical and healthcare environments while still allowing diagnostic and therapeutic procedures to take place in and through the nose and mouth. What is needed is a barrier to air-borne particulates emanating from a subject during a diagnostic and/or therapeutic medical procedure performed in and around the subject's nose and mouth.

SUMMARY OF THE DISCLOSURE

One aspect of the invention provides a method of removing exhaled material from a medical procedure field adjacent to a subject's nose and mouth. In some embodiments, the method includes the steps of: placing an isolation barrier at least partially surrounding the subject's nose and mouth to define the medical procedure field; controlling air flow into the medical procedure field with the isolation barrier; and evacuating air from the medical procedure field at an air evacuation rate greater than or equal to the subject's respiratory minute volume. In some embodiments, the evacuating step includes the step of evacuating air from the medical procedure field at an air evacuation rate greater than or equal to 10 liters/minute.

In some embodiments, the method includes the step of maintaining a negative pressure of 0.14-68 cm $H_2O$ within the medical procedure field. In some such embodiments, the method also includes the step of maintaining a negative pressure within the medical procedure field when the subject coughs or sneezes.

In some embodiments, the method includes the step of filtering air evacuated from the medical procedure field. Some such embodiments may also include the step of returning filtered air to the medical procedure field.

In some embodiments, the placing step includes the step of placing the isolation barrier against a face of the subject, the medical procedure field being bordered by the isolation barrier and the subject's face. Some such embodiments also include the step of establishing a seal between the isolation barrier and the face. In embodiments in which the isolation barrier further includes a drape, the placing step may also include the step of placing the drape against a neck of the subject.

Another aspect of the invention provides a method of performing a procedure in or around a subject's nose or mouth. In some embodiments, the method includes the steps of: evacuating air from within an isolation barrier at least partially defining a medical procedure field adjacent to the subject's nose and mouth at an air evacuation rate greater than or equal to the subject's respiratory minute volume, the isolation barrier controlling air flow into the medical procedure field; and accessing the subject's nose or mouth within the medical procedure field to perform the procedure.

In some embodiments, the evacuating step includes the step of evacuating air from the medical procedure field at an air evacuation rate greater than or equal to 10 liters/minute.

Some embodiments add the further step of maintaining a negative pressure within the medical procedure field. In some such embodiments, the a negative pressure of 0.14-68 cm $H_2O$ is maintained within the medical procedure field. Some embodiments maintain a negative pressure within the medical procedure field when the subject coughs or sneezes.

In embodiments in which the isolation barrier has a transparent portion through which the medical procedure field can be viewed, the viewing step may include the step of viewing the subject's nose or mouth through the transparent portion of the isolation barrier.

Some embodiments include the further step of filtering air evacuated from the medical procedure field. In some such embodiments, the filtered air is returned to the medical procedure field.

In some embodiments, the accessing step includes the step of inserting an instrument through a port in the isolation barrier. In some such embodiments, the inserting step includes the step of inserting the instrument through a seal of the port.

In embodiments in which the isolation barrier includes a drape, the accessing step may include the step of reaching beneath the drape.

Yet another aspect of the invention provides a system for creating an isolated medical procedure field around a subject's nose and mouth. In some embodiments, the system includes: an isolation barrier adapted to at least partially surround the subject's nose and mouth to form the medical procedure field, the isolation barrier having an air exit port; and an air mover operatively connected to the air exit port and configured to remove air from the medical procedure field at an air evacuation rate greater than or equal to the subject's respiratory minute volume. In some embodiments, the air evacuation rate is greater than or equal to 10 liters/minute. In some embodiments, the air mover is further adapted to cooperate with the isolation barrier to maintain a negative pressure within the medical procedure field.

In some embodiments, the isolation barrier has a seal adapted to seal against the subject's face. In some embodiments, the isolation barrier has a drape adapted to be placed against the subject's neck.

In some embodiments, the isolation barrier has an instrument access port arranged and configured to permit a user to insert an instrument to the subject's nose or mouth. In some such embodiments, the instrument access port has a seal adapted to seal around an inserted instrument.

In some embodiments, the isolation barrier further has an air inlet port.

In some embodiments, the isolation barrier is arranged and configured to provide a laminar airflow pattern through the medical procedure field.

In some embodiments, the isolation barrier has a transparent portion through which the medical procedure field can be viewed.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The present invention is generally directed towards systems and methods for creating an isolated medical procedure field using an isolation barrier around at least a subject's nose and/or mouth and evacuating air from the medical procedure field at a rate equal to or greater than the subject's respiratory minute volume to create a negative pressure in the medical procedure field. Medical procedures can be performed in and around the subject's nose or mouth by, e.g., inserting in instrument through a port of the isolation barrier or by reaching around a portion of the isolation barrier, such as a drape.

Figure 1:
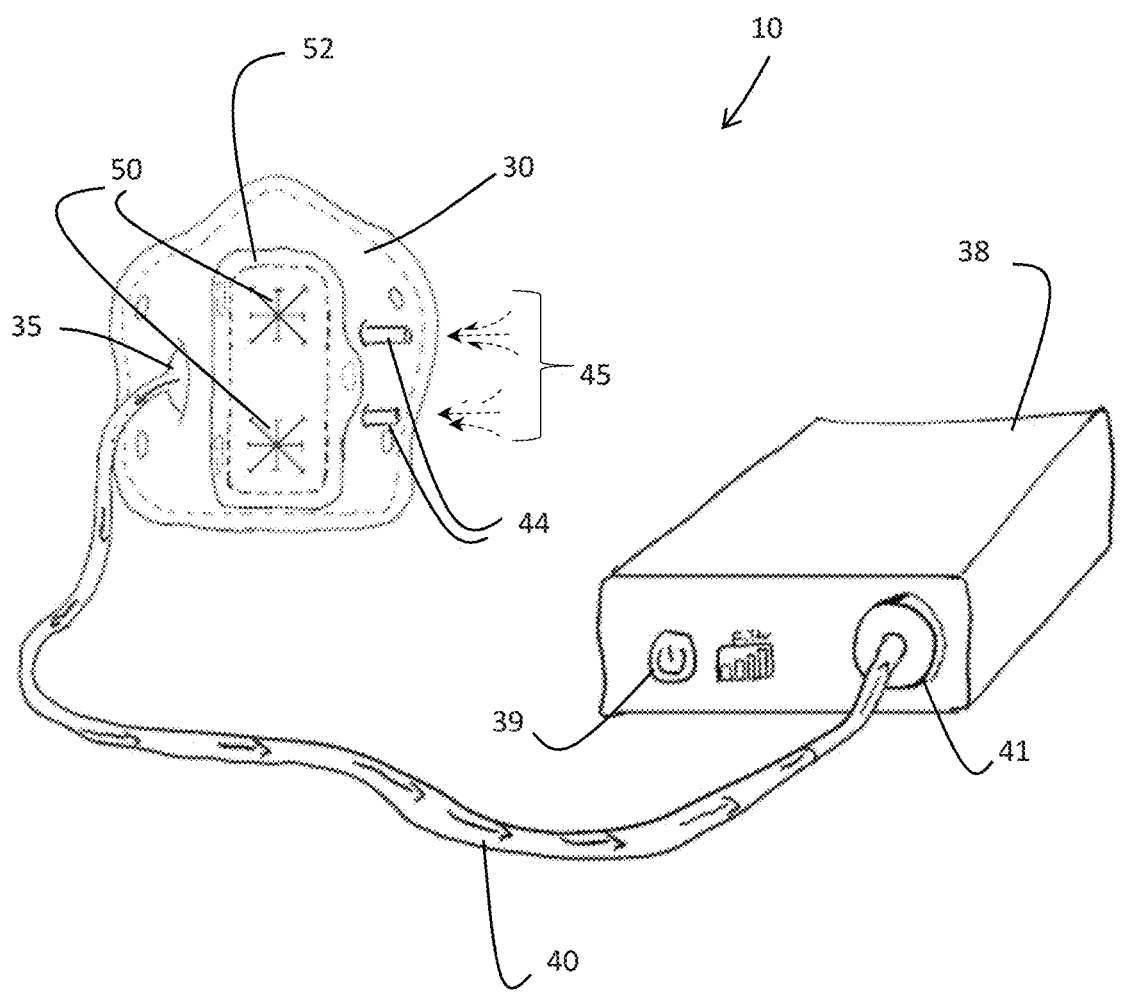
FIG. 1 is a perspective view of a system for creating an isolated medical procedure field around a subject's nose and mouth according to one embodiment of the invention.
Figure 2:
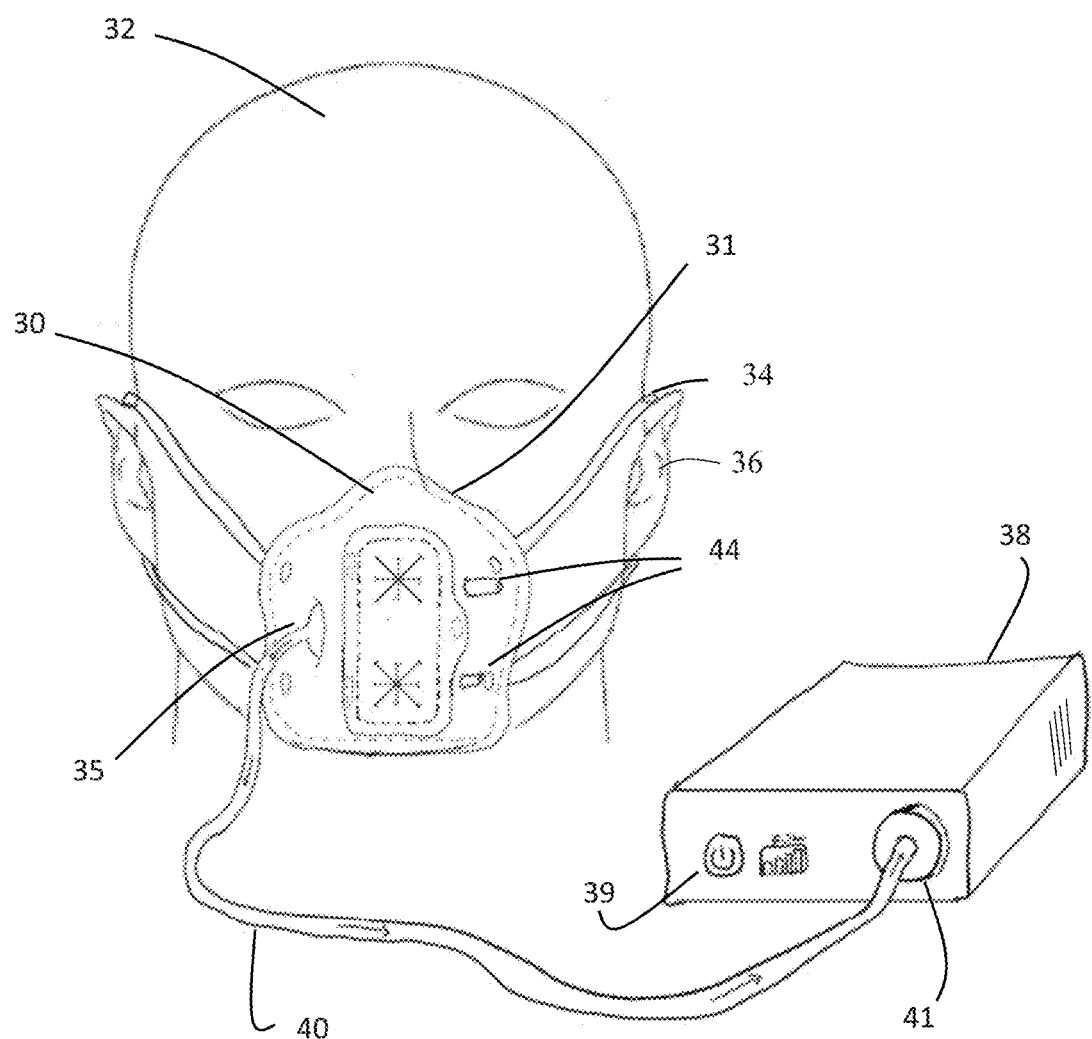
FIG. 2 is a perspective view of the system of FIG. 1 with the isolation barrier in place on a subject to create the medical procedure field.

FIGS. 1 and 2 show an embodiment of a system 10 according to an embodiment of the invention. An isolation barrier 30 such as a mask may be placed and held against the face of the subject 32 (using, e.g., bands 34 that go around the subject's ears 36). In this embodiment, isolation barrier 30 covers the subject's nose and mouth. Edges of the isolation barrier 30 mate with the surface of the subject's face to provide a seal, optionally using, e.g., seals 31 on the inside surface of the mask, to form a medical procedure field between the mask and the subject's face. In this embodiment, the air mover is a fan in housing 38. The fan connects to the interior of the isolation barrier 30 via a mask outlet 35 and an outlet hose 40 of the air management system. In this embodiment, the fan generates volumetric flowrates at least greater than 10 liters/min (e.g., greater than 30 liters/min or greater than 50 liters/min) so as to evacuate air from inside the isolation barrier at a rate higher than the subject's exhalation rate (often defined as the subject's "respiratory minute volume"), thereby creating a negative pressure between the inside of the isolation barrier and the subject's face. The air mover may include a user interface 39 as well as data storage, a control system, communication components (e.g., WiFi, Bluetooth), a controller running software, and/or a battery or other power source.

Figure 3:
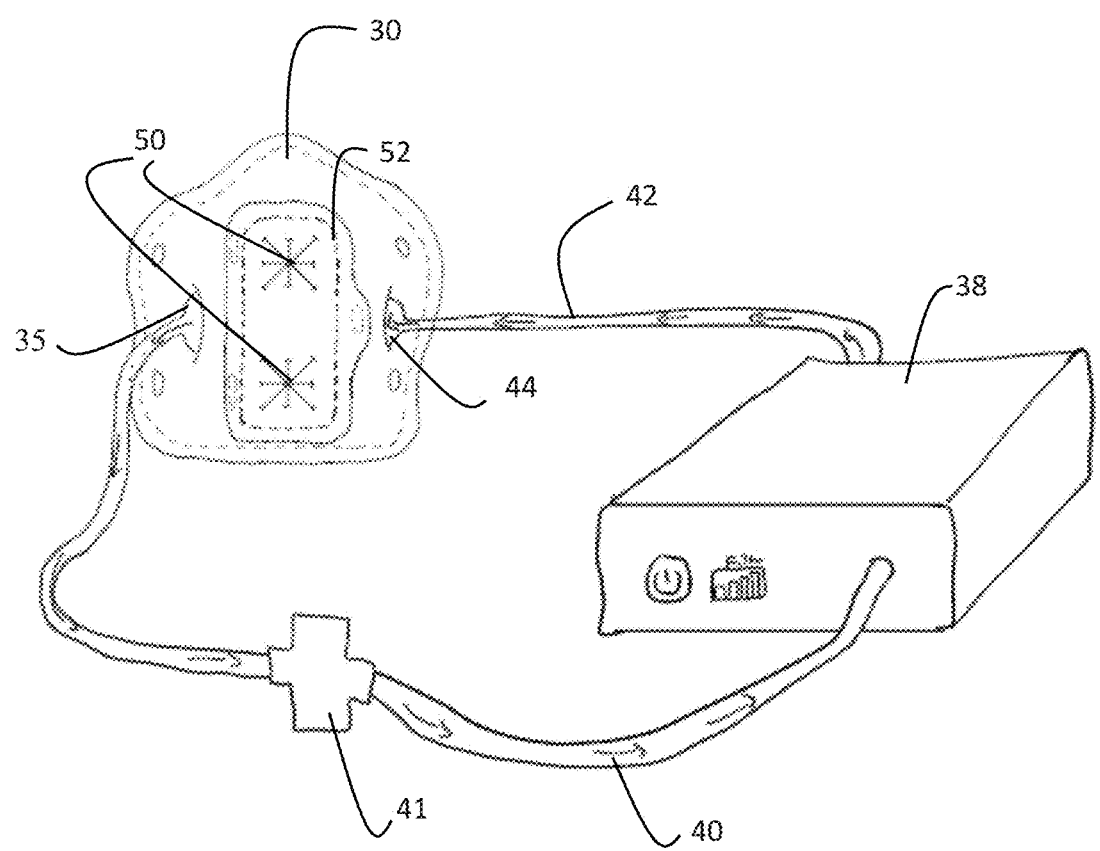
FIG. 3 is a perspective view of a system for creating an isolated medical procedure field around a subject's nose and mouth according to another embodiment of the invention.
Figure 25:
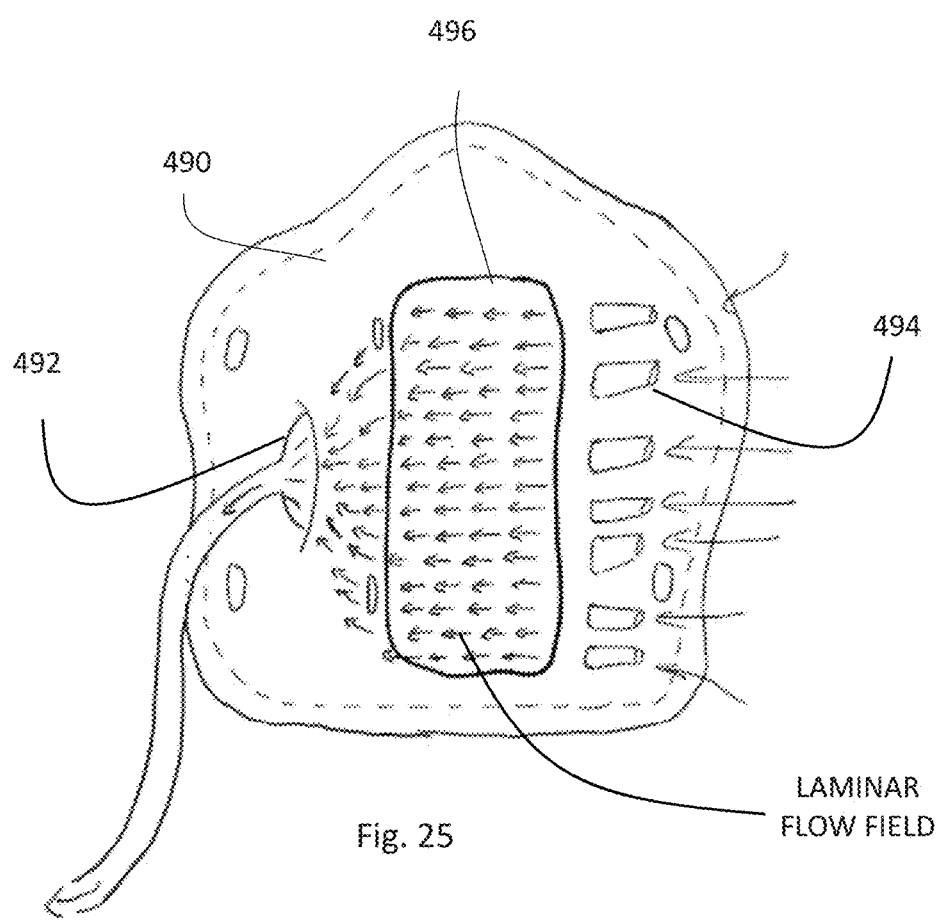
FIG. 25 illustrates an isolation barrier according to an embodiment of this invention with a laminar airflow pattern through the medical procedure field.

In the embodiment of FIGS. 1 and 2, the air mover may exhaust the filtered air into the room after going through a filter 41, and the isolation barrier allows air in through openings 44 in the isolation barrier, as shown by arrows 45 in FIG. 1. The number of openings 44 may be increased to, e.g., provide laminar flow through the medical procedure field, as shown in FIG. 25. In the embodiment of FIG. 3, the air is filtered by a filter 41 in the outlet hose 40, (or within housing 38 or within inlet hose 42), and the filtered air is returned to medical procedure field via an inlet hose 42 and one or more ports 44.

In these embodiments, two access ports 50 are disposed on the front of isolation barrier 30. Access ports 50 may be formed of slits in resilient material to permit insertion of instruments and/or diagnostic tool at the desired sagittal or coronal angles, seal around those instruments and tools while they are being used, and seal completely after removal of the tools. In addition, the access ports 50 may be in one or more optional removable flaps 52 that can be opened to provide a larger access port for wider access to the subject's nose and/or mouth. When flap 52 is removed, the air flow from the air mover is sufficiently high to maintain a negative pressure in the medical procedure field to capture and remove any droplets or particulates in the subject's exhaled breath.

The air mover is designed to produce these flowrates with minimal noise pollution having a sound rating less than 60 dBA, preferably less than 50 dBA. In some embodiments, the air mover also has sensors that monitor the system and isolation barrier. Examples of parameters that the system will monitor are pressure, temperature, humidity, and particulate count. The system also has ways of retrieving this data for reporting and storing. Example of retrieving data is physical connection (e.g., USB) and/or wireless transmission (e.g., Bluetooth).

In some embodiments, the filter 41 is, for example, a one sub-micron (preferably <0.3 µm) particulate filter (e.g., HEPA, ULPA, Charcoal). In some embodiments, the air management system has fittings and hosing that are connectable to the isolation barrier.

In some embodiments, the exterior of the mask fits snuggly on the bridge of the nose, the cheeks, and chin of the subject and is secured to the face by straps that go around the head or around the ears of the subject. The apparatus contacts the nose on the lateral nasal cartilage and/or nasal bone without touching the major alar cartilage (tip of the nose) so that the tip of the nose can be manipulated (e.g., flexed upward, stretched) with nasal instruments as needed during nasal procedures.

The sagittal angle of access area provides greater than 60 degrees (preferably greater than 70 degrees) of instrumentation movement in the sagittal plane from the base of the nostril (nasal sill) upwards and greater than 10 degrees in either direction from the center of the nose (septum) in the coronal plane while minimizing the potential of subject particulates exiting the subject air environment via exhalation, sneezing or coughing. These degrees of freedom are important to allow the physician to visualize and treat the target sites like the frontal recess, posterior ethmoids, and the nasopharynx.

The contact points of apparatus on the chin and cheeks allow the mouth to open without losing the local barrier. In some embodiments, this is achieved by the exterior of the barrier just resting on the cheeks and chin allowing movement of the face and the high-volume evacuation flowrate prevents particulates from escaping during the movement and in other embodiments the mask is designed fit and move with the chin and cheeks as the mouth is opened and closed.

Figure 4:
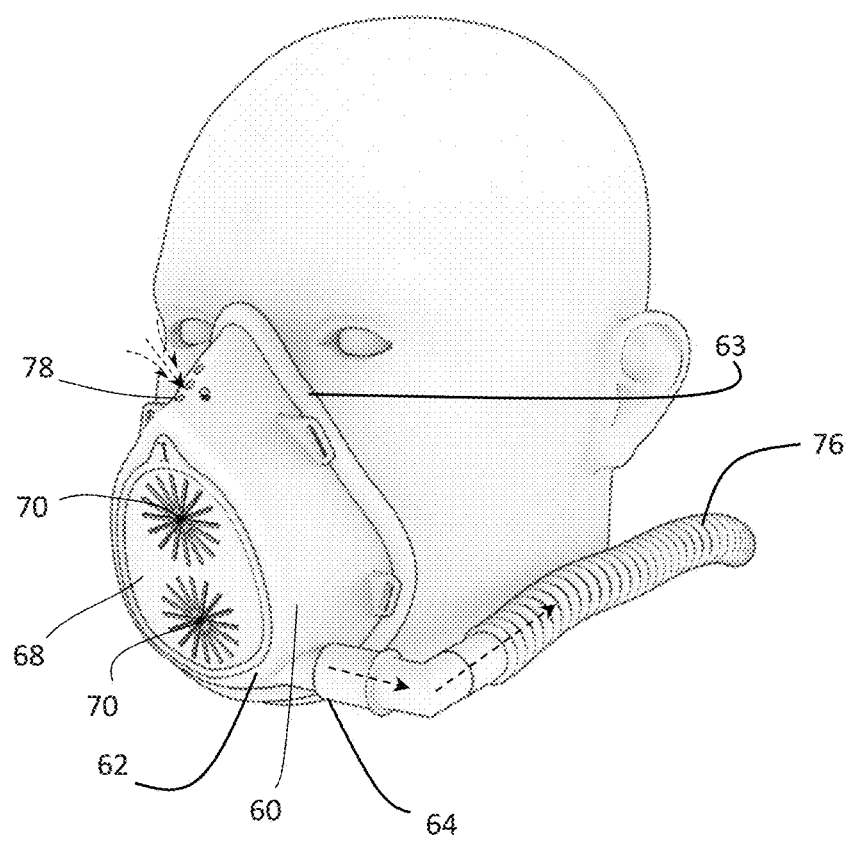
FIG. 4 is a perspective view of an isolation barrier for use in a system for creating an isolated medical procedure field around a subject's nose and mouth according to another embodiment of the invention, in place on a subject to create the medical procedure field.
Figure 5:
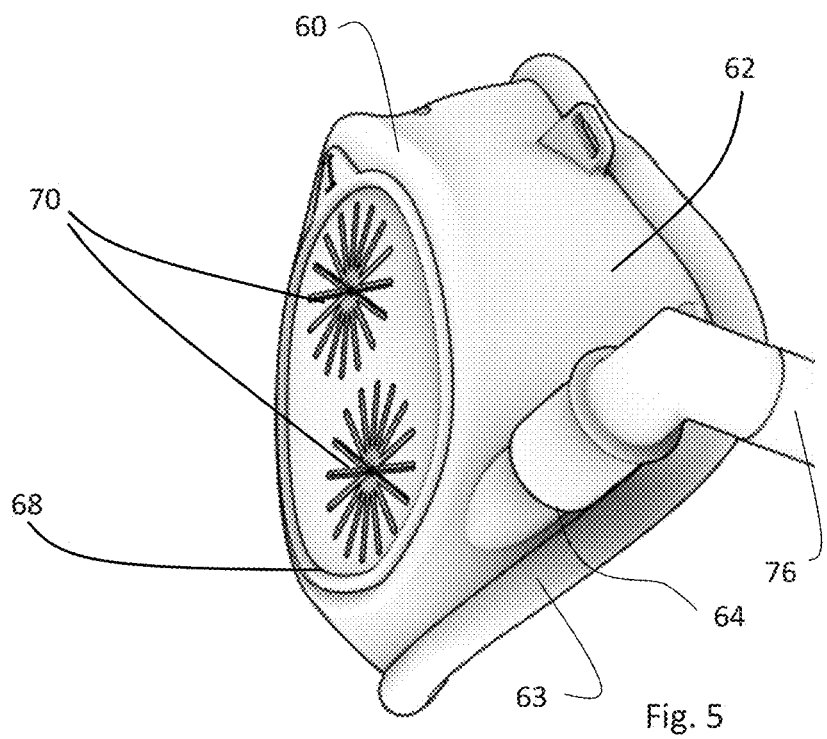
FIG. 5 is a perspective view of the isolation barrier of FIG. 4.
Figure 6:
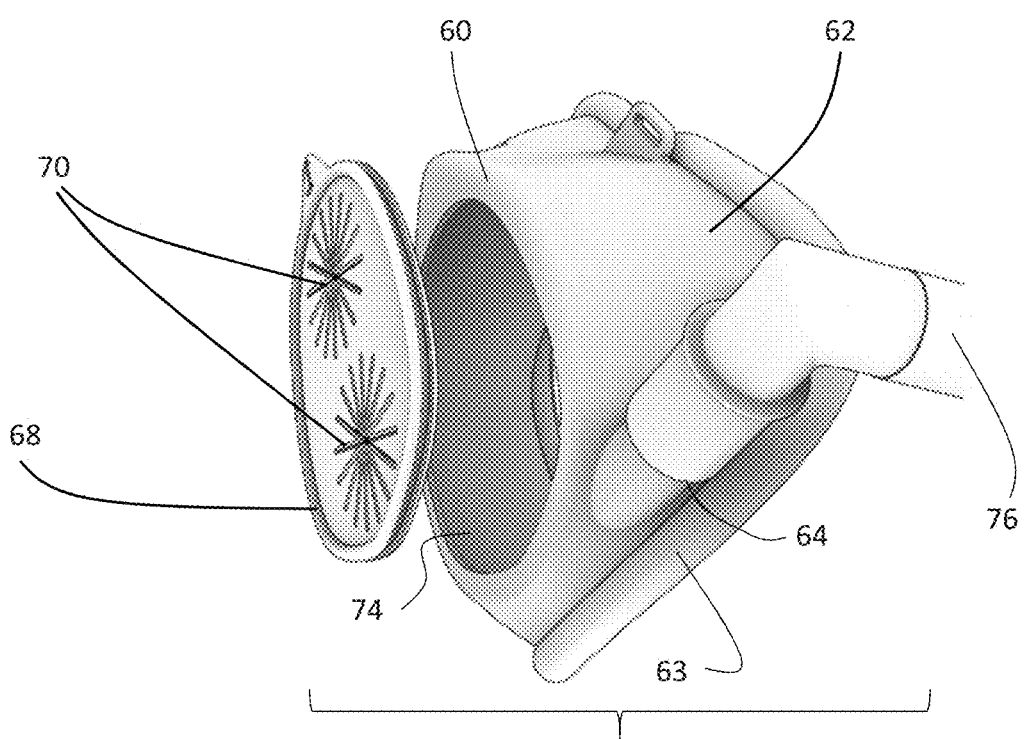
FIG. 6 is a perspective view of the isolation barrier of FIGS. 4 and 5 showing a removable patch removed.

FIGS. 4-6 show another embodiment of this invention. In this embodiment, isolation barrier 60 has a clear plastic shell 62 (e.g., made from polycarbonate, polyethylene, PVC) surrounded by a seal 63. Bands (not shown) may attach the isolation barrier to the subject's ears or go around the subject's head to create a medical procedure field between shell 62 and the subject's face. The clear material of shell 62 permits the medical procedure field to be viewed by a healthcare provider. Various patches (such as a flat rubber patch 68 with sealable openings 70) can attach to barrier 60 via a seal (e.g., gel) around an opening 74.

A hose 76 leads from a port 64 in shell 62 to an air mover, such as a fan (not shown). Instead of returning filtered air to the isolation barrier, these embodiments provide air holes 78 in the isolation barrier for the subject's inhaled air, as shown by the arrows in FIG. 4. When patch 68 is removed to enable the clinician to access the medical procedure field through opening 74 to perform a procedure (e.g., on or in the subject's oral cavity or nasal cavity), the air flow out of port 64 created by the air mover is sufficiently high to maintain a negative pressure in the medical procedure field to capture any droplets or particulates in the subject's exhaled breath.

Figure 7:
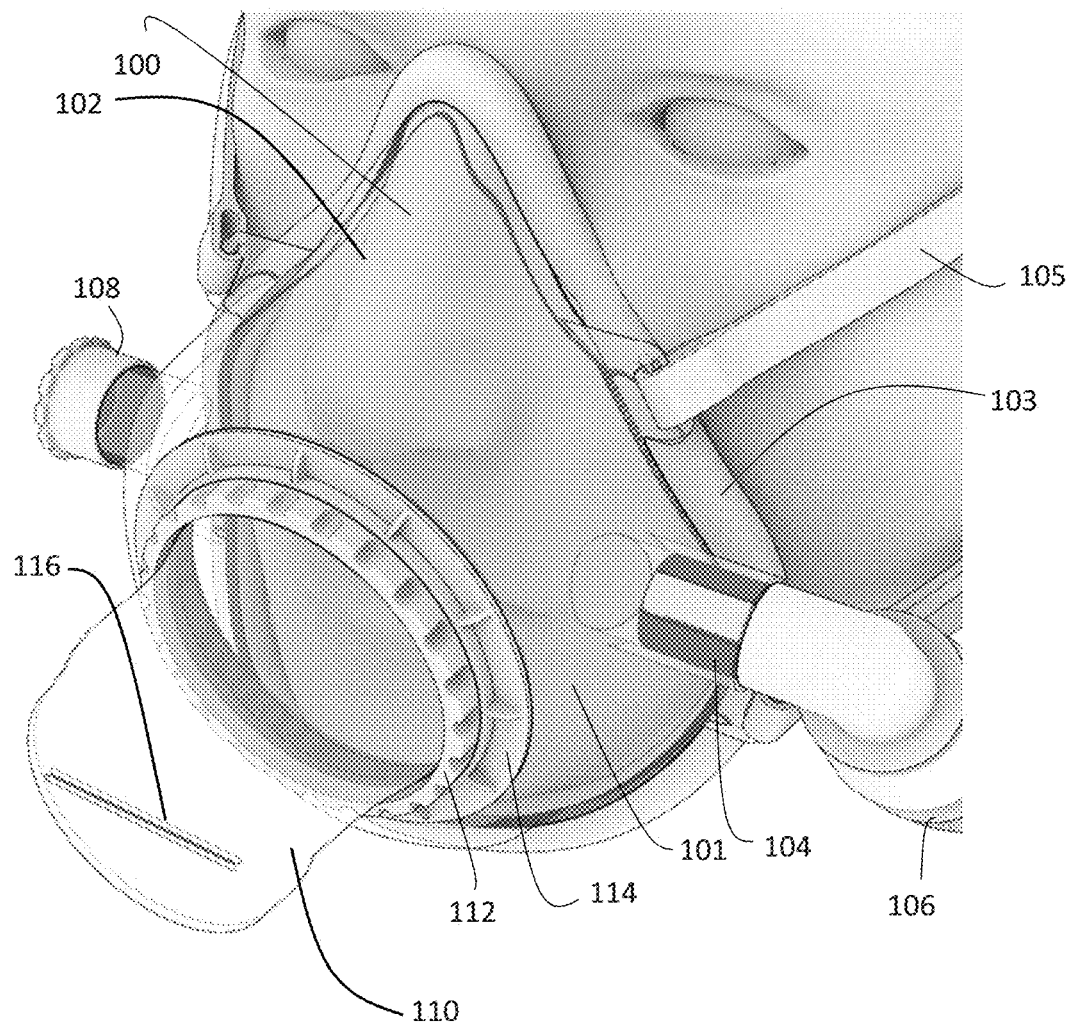
FIG. 7 is a perspective view of an isolation barrier for use in a system for creating an isolated medical procedure field around a subject's nose and mouth according to yet another embodiment of the invention, in place on a subject to create the medical procedure field.
Figure 8:
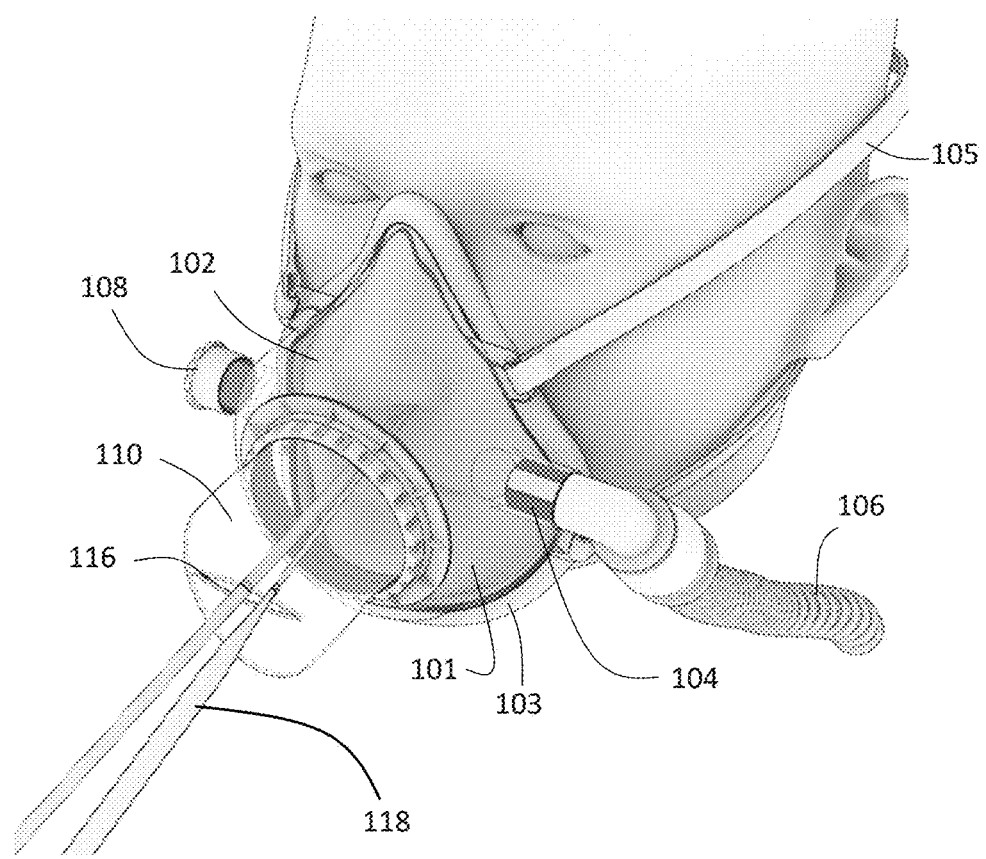
FIG. 8 is a perspective view of the isolation barrier of FIG. 7 showing medical instruments being inserted into the medical procedure field.

FIGS. 7 and 8 show another embodiment of the invention. In this embodiment, the isolation barrier 100 includes an expandable portion that can accommodate a sudden increase in the volume and/or momentum of a subject's exhalation, such as from a cough or a sneeze, without breaking the seal of the isolation barrier around the subject's face and thereby exposing a caregiver to aerosols in the medical procedure field. As in other embodiments, isolation barrier 100 has a clear plastic shell 102 (e.g., made from polycarbonate, polyethylene, PVC) surrounded by a seal 103. Bands 105 may attach the isolation barrier to the subject's ears or go around the subject's head to create a medical procedure field 101 between shell 102 and the subject's face. A hose 106 leads from a port 104 in shell 102 to an air mover, such as a fan (not shown). Air enters the medical procedure field through inlet port 108. Inlet port 108 may have a filter.

A collapsible inflatable bag 110 made of thin-walled plastic film is disposed in the shell 102. Bag 110 may expand to capture a sneeze event and prevent a pressure increase from a sneeze or a cough from escaping the isolation barrier. After the cough or sneeze, the negative pressure within the medical procedure field behind the shell 102 deflates bag 110 as the exhalation, particulates, pathogens and/or aerosols are removed from the isolation barrier by way of the airflow outlet port 104. A slit 116 in bag 110 permits the insertion of a tool 118 for performing a procedure in the medical procedure field, as shown in FIG. 8. Bag 110 may be detached from shell 102 by disconnecting connectors 112 and 114 on the bag and shell, respectively, to replace the bag or to leave an opening for accessing the medical procedure field. Other embodiments may employ one or more of: expandable or inflatable bags; elastomeric balloons; bellows; or other containment elements capable of rapid expansion under low pressure increases in the event of an episodic event.

Figure 9:
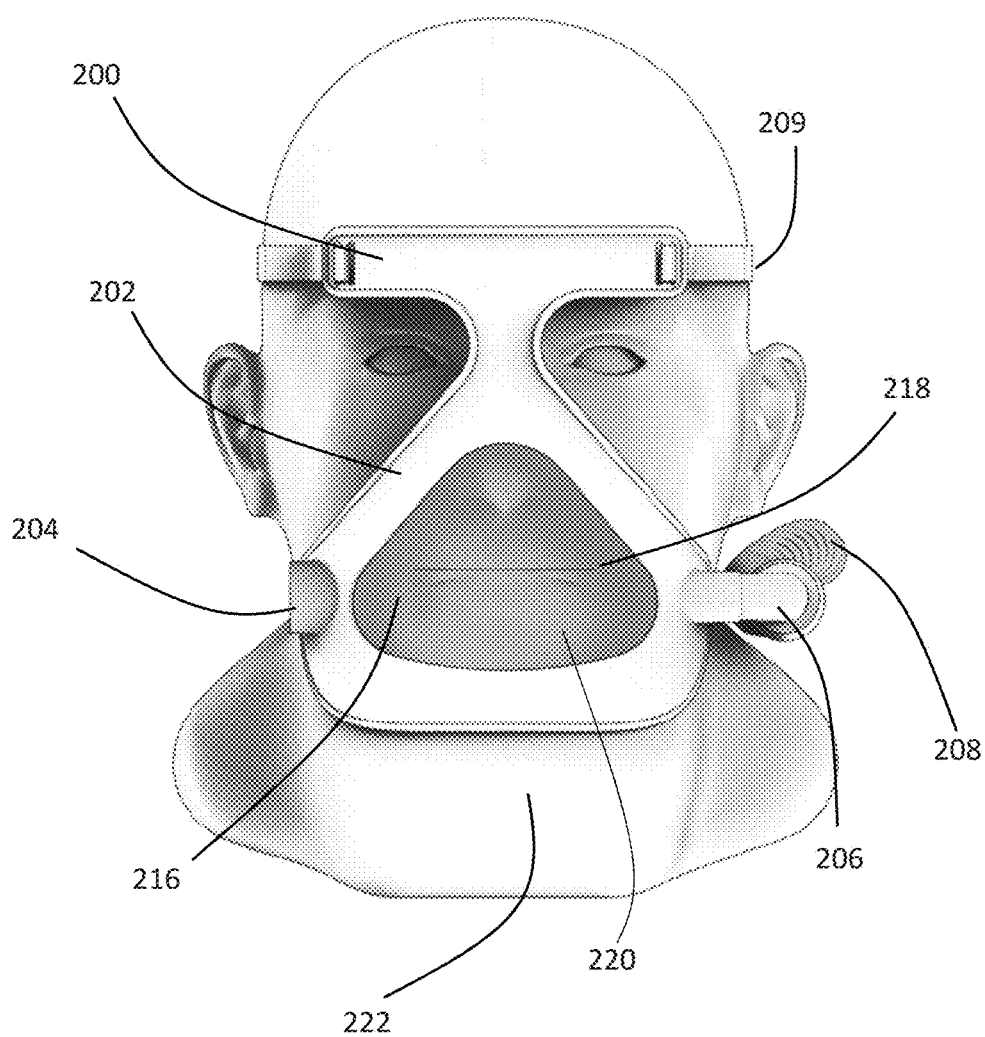
FIG. 9 is a front elevational view of an isolation barrier for use in a system for creating an isolated medical procedure field around a subject's nose and mouth according to yet another embodiment of the invention, in place on a subject to create the medical procedure field.
Figure 10:
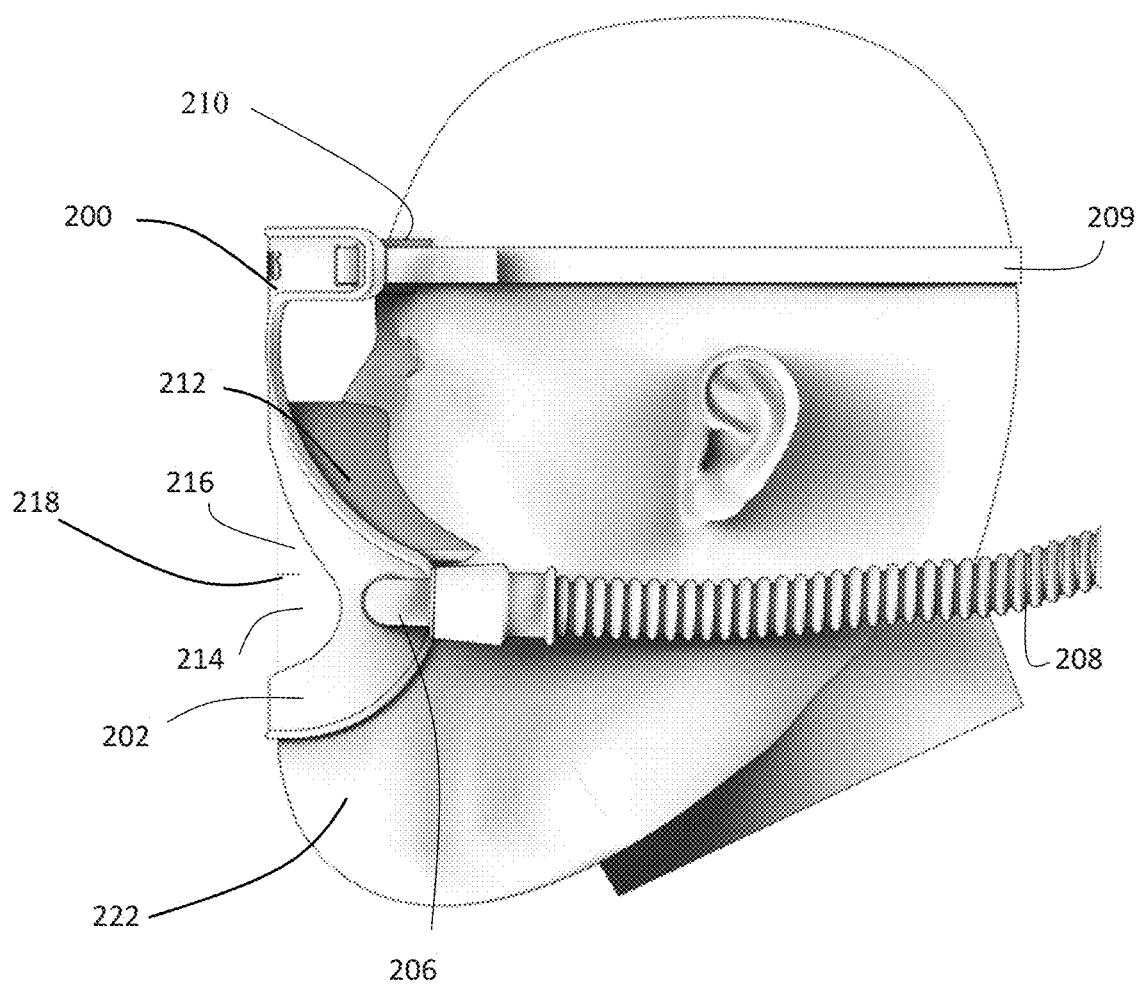
FIG. 10 is a side elevational view of the embodiment of FIG. 9.
Figure 11:
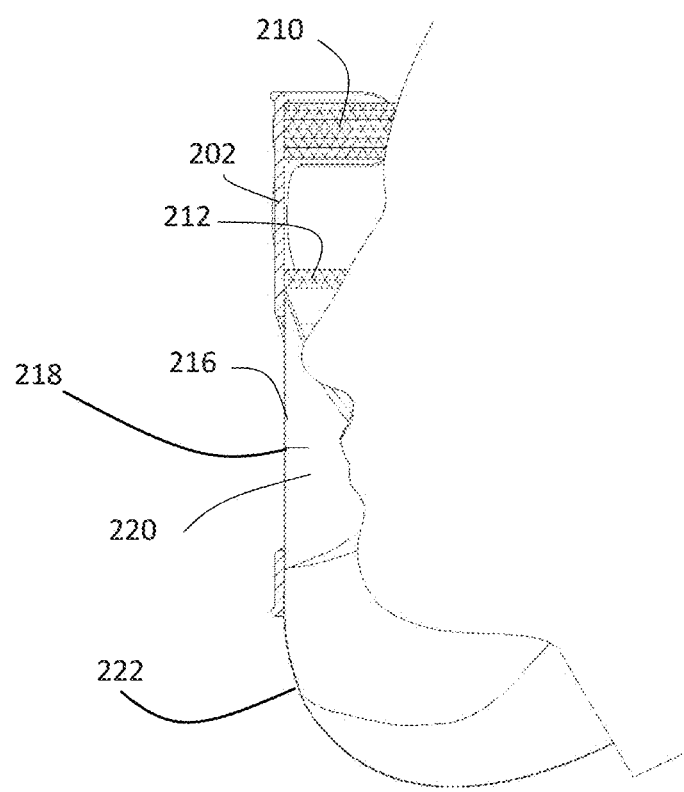
FIG. 11 is side sectional view of the embodiment of FIGS. 9 and 10.

FIGS. 9-11 show yet another embodiment of the invention. Isolation barrier 200 provides a "one-size-fits-all" configuration that accommodates a large array of facial geometries, facial hair, facial sizes, facial deformities, etc., and provides unobstructed movement of the jaw while preventing aerosols from escaping, so as to allow the subject to open and close his mouth without compromising the barrier integrity. Isolation barrier 200 has a support structure 202 with built-in inflow port 204 and outflow port 206. Support structure 202 and ports 204 and 206 may be injection molded. Ports 204 and 206 may be equipped with air filters to filter the air going into and coming out of isolation barrier 200. In one optional embodiment, the ports 202 and 204 may be the same size to enable the air flow conduit 208 connected to an air mover (not shown) to be placed on either side. Straps 209 attach the isolation barrier to the subject's head.

A forehead pad 210 affixed to the top of the isolation barrier and a midface pad 212 affixed to the midportion of the isolation barrier are made of compliant material (e.g., open-cell or closed-cell foam or a compliant polymer) to provide a secure and comfortable seal around the subject's face. The pads may be affixed via, e.g., adhesive or mechanical compression. Alternatively, the pads 210 and/or 212 may be highly compliant inflatable bladders filled with air at the time of use to conform to the subject's face. When the isolation barrier 200 is placed on the subject's face, the forehead pad 210 makes contact and conforms to the subject's forehead and the midface pad 212 conforms to the bridge of the nose and cheeks of the subject, as shown in FIG. 10. These pads stabilize the isolation barrier on the subject, while the midface pad additionally creates a sufficient seal on the bridge of the nose and the cheeks without contacting the anterior portion of the nose, allowing the tip of the nose move freely (such as my be required in some medical procedures).

Isolation barrier 200 has an access window 214 adjacent to the nose and mouth. An insert 216 may be placed in window 214 to close the opening, and one or more ports 218 in insert 216 may permit the insertion of tools to perform medical procedures in the medical procedure field 220 defined by the isolation barrier 200 and the subject's face. Insert 216 and instrument access port(s) 218 allow access to the subject's nose and/or the mouth while preventing particulates, pathogens and aerosols from escaping the medical procedure field 220 during normal breathing or during an episodic event such as a sneeze or a cough. Insert 216 may be removed while active airflow is being pulled from the mask giving open access to the nose and mouth and creating an airflow pattern serving to prevent the escape of particulates, pathogens and aerosols from escaping the isolation barrier.

A drape 222 extends from the bottom of the support structure 202 and may be placed against the lower part of the subject's face and around a portion of the subject's neck, as shown in FIGS. 9-11. Drape 222 may be affixed to support structure 202 via, e.g., stitching, thermal stacking or adhesive. Drape 222 may be made of a thin flexible polymer film such as urethane, silicone or other polymer, or of a woven or non-woven fabric such as Tyvek or the like. The drape 222 is sized to accommodate all jaw geometries, necks, facial hair, and to be loose and baggy. Around the perimeter of the drape is an elastic band (not shown), sewn into the drape, allowing the drape to form a seal around the face and neck. This seal formed by the drape may be sufficient to prevent the exchange of airflow across it, or it may affect a partial seal only, allowing negative pressures within the medical procedure field to draw air flow through the drape seal in such a manner as to prevent the escape of particulates, pathogens and aerosols around the drape.

In one use scenario, the isolation barrier 200 is placed around the subject's forehead, and the drape is tied around the subject's neck with the elastic band or another attachment means. The subject is then asked to wait in the waiting room of the physician's office or other healthcare facility. In this passive (non-powered) state wherein the isolation barrier is not connected to an air mover, the isolation barrier serves as a surgical mask comprising air filters on the inlet and outlet air flow ports as well as the instrument access port seal to maintain a seal. When the subject enters the exam room and sits down, the healthcare worker then attaches the air outlet conduit (that is attached to the filter, which in turn is attached to the air mover) to the isolation barrier and turns on the air mover, starting the flow of air. The high volumetric airflow begins replacing air inside the isolation barrier with air from the room, moving the air within the isolation barrier into the air conduit through the filter into the air mover, filtering the air and releasing it back into the room. The healthcare worker then begins the medical procedure by placing the instruments through the access port breaking the seal of the port and inserting the instrument into the airway cavity. During this procedure, the aerosolization caused by the manipulation of the airway tissue is captured by the airflow pattern, evacuated from the isolation barrier through the air outlet port, passed through the airflow conduit and filtered before allowing the air to release back into the room. After the procedure is complete, the local area protection device is run for several minutes, allowing the air in the isolation barrier to change multiple times. The isolation barrier is then detached from the air conduit and the subject can leave with the isolation barrier in the non-powered state.

In some embodiments, the midface pad runs completely around the nose and the mouth creating a seal and stabilizing the isolation barrier on the bridge of the nose, cheeks, and chin. In other embodiments, the portion of the support structure above the eyes and forehead pad are removed and the attachment straps are affixed to the mid portion of the isolation barrier. The forehead and midface pad depth and conformability are sufficient to accommodate various sizes of noses, foreheads, and cheek bones. The clearance range is 2 to 100 mm (preferably 30-70 mm). This depth range serves to accommodate a large range of facial geometries while still ensuring the isolation barrier doesn't impede instrument access or prevent a healthcare worker from reaching within the nasal or oral cavity. The height range of the pads are typically between 2 mm and 50 mm, allowing sufficient seal without blocking access to the nose or mouth. The pads may comprise uniform cross sectional geometry and/or dimensions, or they may vary along the length of the pads. The pads may also be customizable by a healthcare worker to create a custom fit to the patient in some embodiments. In some embodiments a pocket may be formed in or affixed to the drape.

The isolation barrier systems of the invention are configured to create airflow patterns in the vicinity of the patient's face, and more specifically in the vicinity of the patient's nose and/or mouth. These airflow patterns act to capture and transport normal and episodic respiratory exhalations, as well as any associated particulates, pathogens and aerosols emitted by said patient, from the vicinity of the nose or mouth, in a controlled manner toward one or more airflow outlet ports, into one or more airflow conduits, and away from the isolation barrier to be filtered and collected for later disposal.

Figure 12:
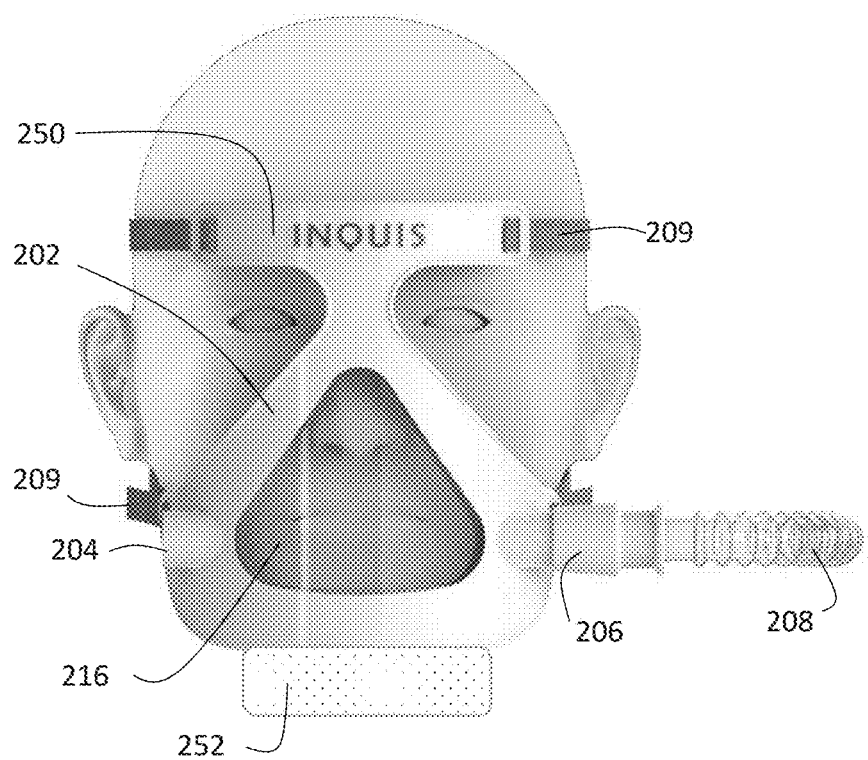
FIG. 12 is a front elevational view of an isolation barrier for use in a system for creating an isolated medical procedure field around a subject's nose and mouth according to still another embodiment of the invention, in place on a subject to create the medical procedure field.

The isolation barrier 250 in the embodiment of FIG. 12 is a modification to the embodiment of FIGS. 9-11 that replaces the drape with a pouch 252 to catch removed tissue or other debris. Pouch 252 also serves as an expansion chamber to accommodate sudden increases in pressure and flow from the subject due to a cough or sneeze. Other elements of the isolation barrier remain the same and therefore retain the same element numbers.

Figure 13:
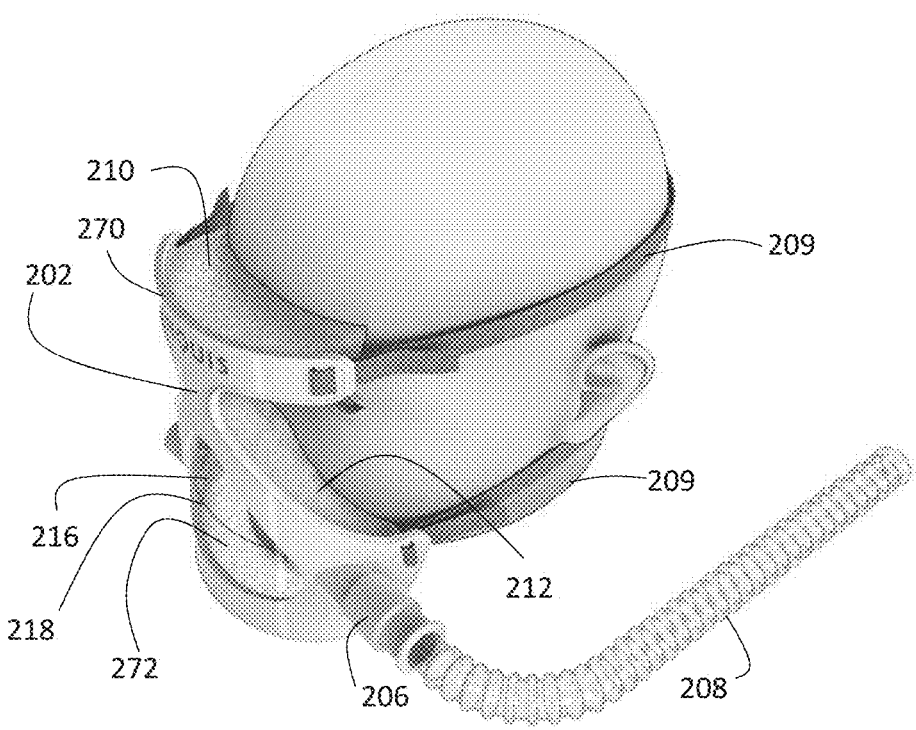
FIG. 13 is a perspective view of an isolation barrier for use in a system for creating an isolated medical procedure field around a subject's nose and mouth according to another embodiment of the invention, in place on a subject to create the medical procedure field.

The isolation barrier 270 of the embodiment of FIG. 13 extends midface pad 212 to a region 272 that rests against the subject's chin. Like the pads 210 and 212, pad 272 may be made of compliant material (e.g., open-cell or closed-cell foam or a compliant polymer) to provide a secure and comfortable seal around the subject's face. The pad may be affixed via, e.g., adhesive or mechanical compression. Alternatively, pad 272 may be a highly compliant inflatable bladder filled with air at the time of use to conform to the subject's face. When the isolation barrier 270 is placed on the subject's face, the forehead pad 210 makes contact and conforms to the subject's forehead, the midface pad 212 conforms to the bridge of the nose and cheeks of the subject, and the chin pad 272 contacts and conforms to the subject's chin, as shown in FIG. 13. These pads stabilize the isolation barrier on the subject. The isolation barrier 270 of FIG. 13 may have an optional pouch, as in the embodiment of FIG.

12, in which case there would be an opening in pad 272 to permit tissue and other debris to fall into the pouch. The other elements of this embodiment are the same as the like-numbered elements of the embodiments of FIGS. 9-11 and FIG. 12.

Figure 14A:
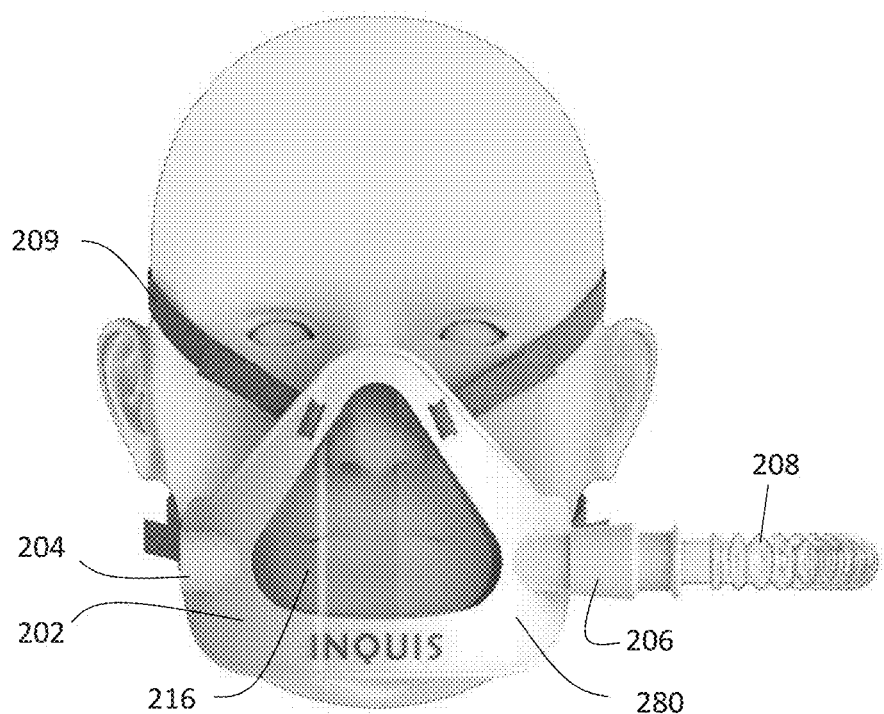
FIG. 14A is a front elevational view of an isolation barrier for use in a system for creating an isolated medical procedure field around a subject's nose and mouth according to yet another embodiment of the invention, in place on a subject to create the medical procedure field.
Figure 14B:
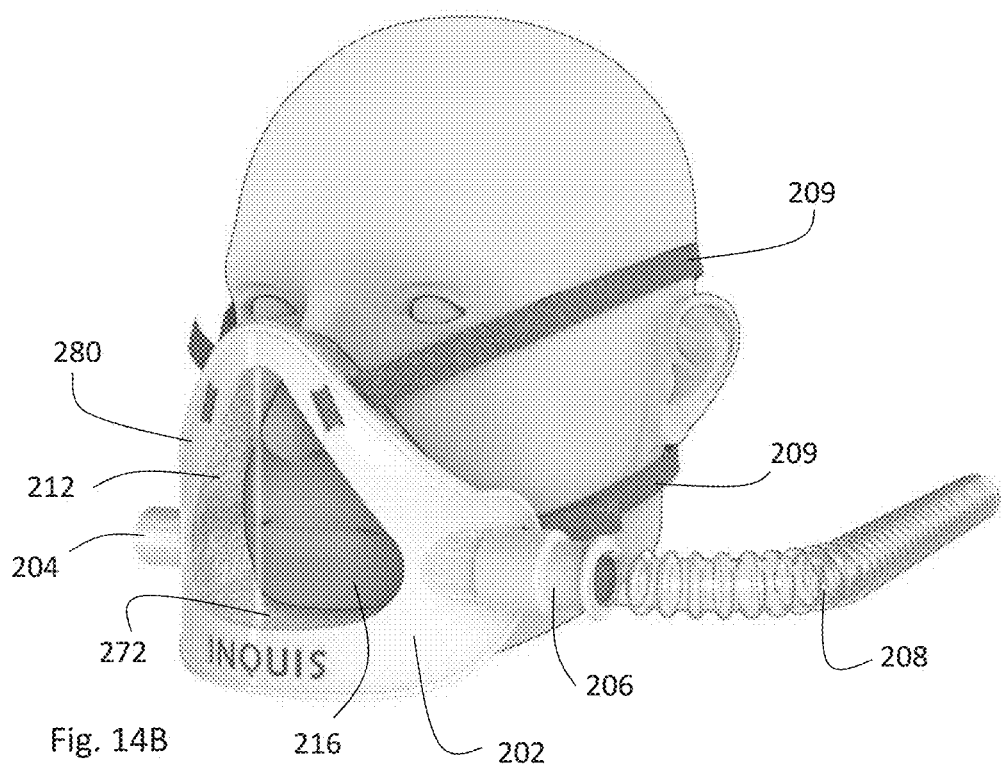
FIG. 14B is a perspective view of the embodiment of FIG. 14A.

The isolation barrier 280 of the embodiment of FIGS. 14A-B is similar to the embodiment of FIG. 13, but it omits the forehead pad and the portion of the support structure 202 extending to the forehead region. The other elements of this embodiment are the same as the like-numbered elements of the embodiments of FIGS. 9-11, FIG. 12 and FIG. 13.

Figure 15:
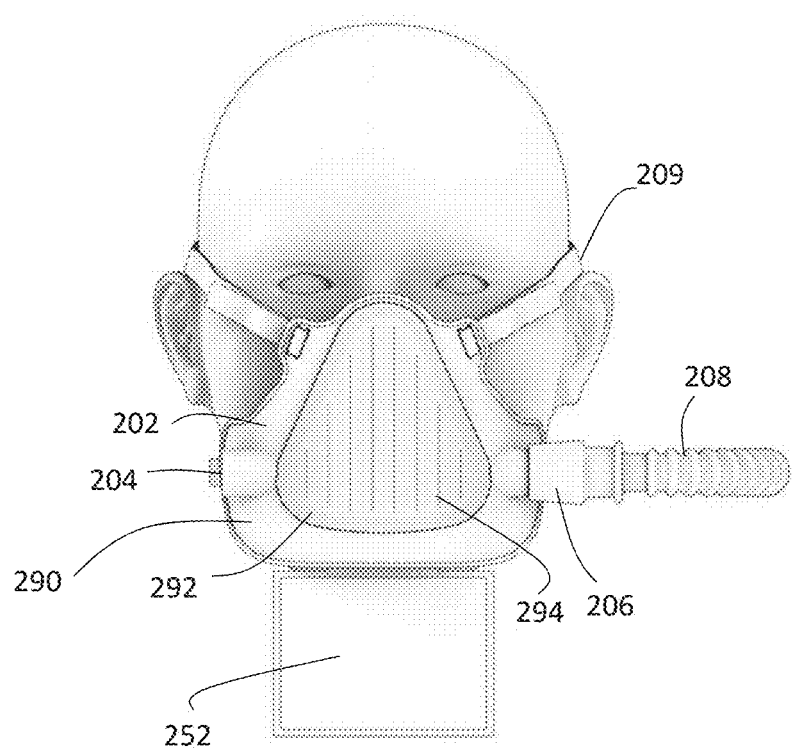
FIG. 15 is a front elevational view of an isolation barrier for use in a system for creating an isolated medical procedure field around a subject's nose and mouth according to still another embodiment of the invention, in place on a subject to create the medical procedure field.

The isolation barrier 290 of FIG. 15 is similar to that of FIGS. 14A-B but replaces the insert in the opening with a transparent insert 292 with multiple slits 294 providing access for tools to perform medical procedures in the medical procedure field. (FIG. 15 shows insert 292 as opaque in order to illustrate the vertical slits 294.) The other elements of this embodiment are the same as the like-numbered elements of the embodiments of FIGS. 9-11, FIG. 12, FIG. 13, and FIGS. 14A-14B.

Figure 16:
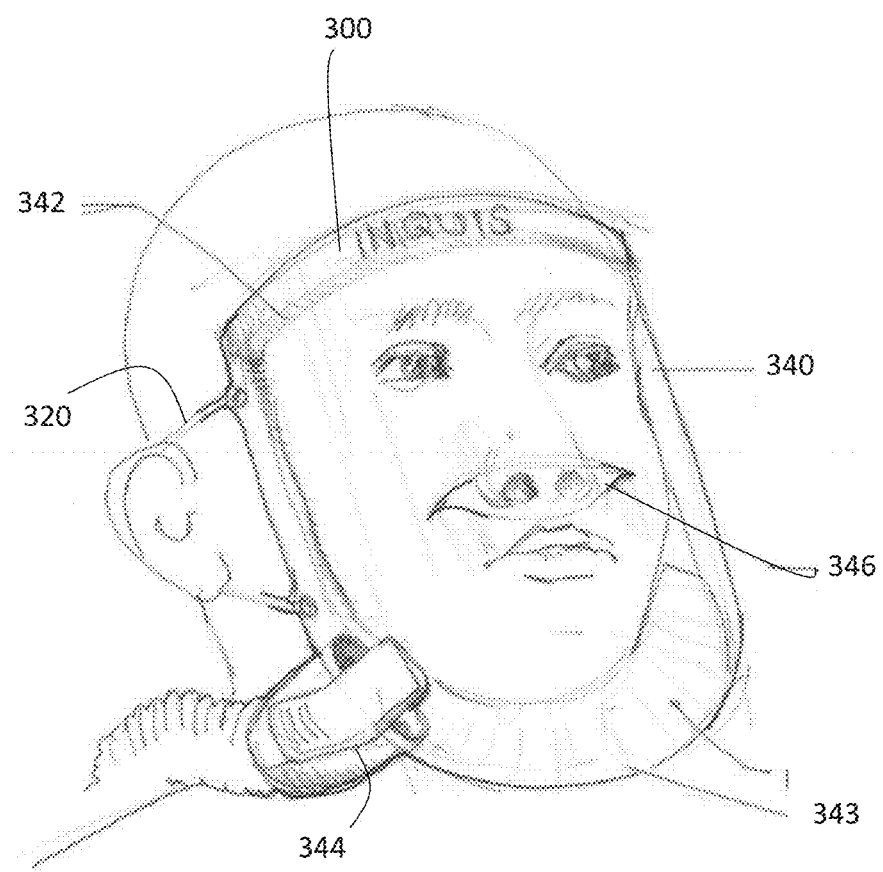
FIG. 16 is a perspective view of an isolation barrier for use in a system for creating an isolated medical procedure field around a subject's nose and mouth according to another embodiment of the invention, in place on a subject to create the medical procedure field.

FIG. 16 shows an isolation barrier 300 that covers the entire face of the subject to protect both the subject and the healthcare specialist from exposure. The isolation barrier 300 has a clear acetate or polycarbonate shield 340, a seal 342 around the top edge, and a foam skirt 343 at the bottom. The seals are made, e.g., of open-cell foam in this embodiment. In other embodiments the seals are made of thin polymeric material such as silicone, polyurethane or latex. The isolation barrier may be held in place by band 320 that go around the subject's ears or head. In some cases, the flat shield 340 can be bent into a semi-cylindrical shape. In others, the shield 340 can be thermoformed into a more ergonomic configuration. A hose 344 leading to an air mover clips on to the shield to provide negative air pressure behind the shield. The seal 342 and/or skirt 343 allow air to enter through the periphery of the shield, filtering out some particulate and airborne droplets. Due to the negative pressure inside the shield 340, the subject's breathing, coughing, etc., does not enter the room air, but is sucked away through the hose 344 through a HEPA filter by the air mover. When placed as shown in FIG. 16, isolation barrier 300 and the subject's face together define a medical procedure field around the subject's nose and mouth. Access to the medical procedure field to perform, e.g., a medical procedure in or around the oral cavity or nasal cavity is gained by means of a slit 346 in the clear portion of the shield, which can be pressed inward by the healthcare specialist to create an opening. When released, this slit portion pops back out to its original shape, sealing the opening in the shield 340. Alternately, the clear portion of the shield can be formed in such a way that the deflected portion is bi-stable. When pressed inward, it stays in that position until pulled outward, where it then stays in the sealed position. The isolation barrier 300 is disposable. The suction hose 344 and clip can be re-used for the subsequent subjects. Periodically, the HEPA filter, suction hose 344, and coupling are replaced to ensure only well filtered air returns to the room environment via the air mover.

Figure 17A:
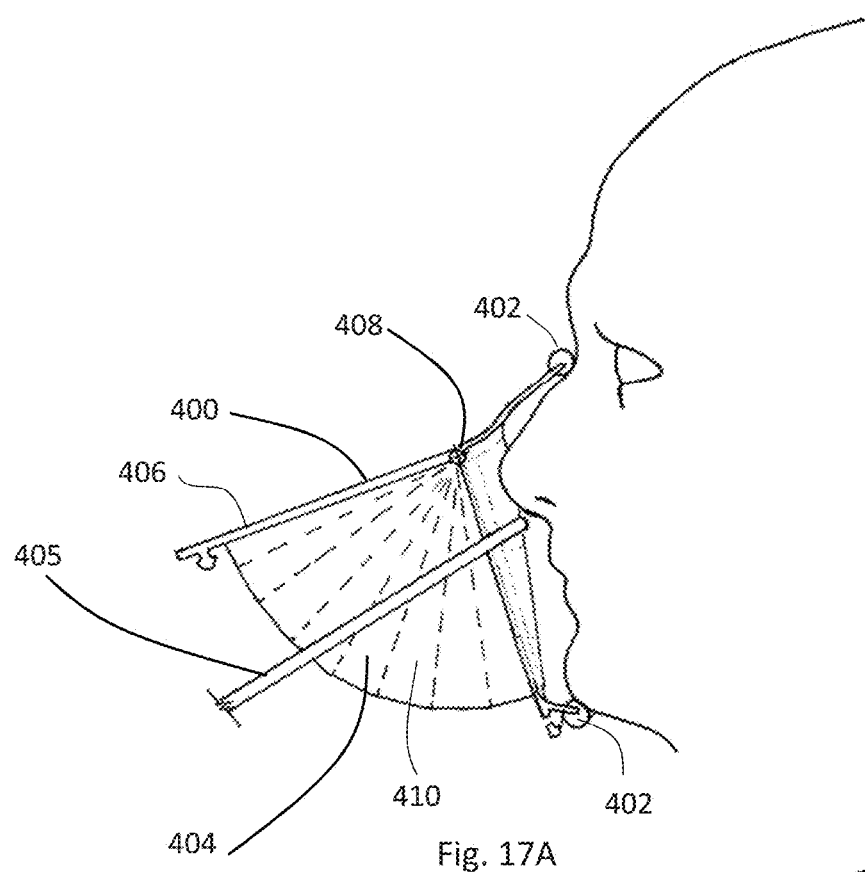
FIG. 17A is a side partially sectional view of an isolation barrier for use in a system for creating an isolated medical procedure field around a subject's nose and mouth according to another embodiment of the invention, in place on a subject to create the medical procedure field, showing the isolation barrier in an open position.
Figure 17B:
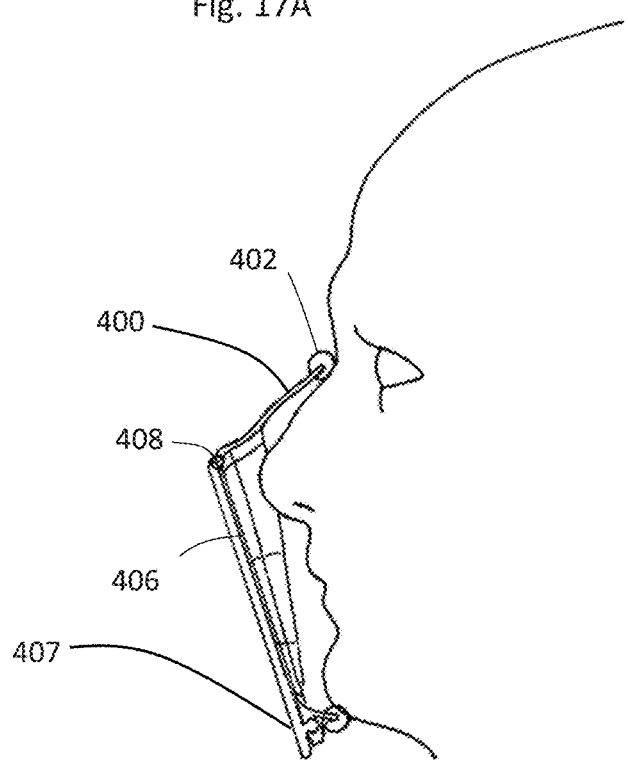
FIG. 17B is a side partially sectional view of the embodiment of FIG. 17A showing the isolation barrier in a closed position.

FIGS. 17A and 17B depict an isolation barrier 400 according to another embodiment of the invention. As in other embodiments, isolation barrier 400 is used with an air conduit (not shown); a filter (not shown); and an air mover (not shown). The support structure of the isolation barrier 400 is made of a clear rigid to semi-conformable polymer such as polycarbonate or transparent polyvinyl chloride. The barrier is designed to conform to the nose, cheeks and the chin or upper neck to create a seal around the perimeter of the barrier. When the support structure is made of a rigid polymer, a sealing component 402 is added to the outer perimeter of the isolation barrier, as described with respect to other embodiments. On the front face of the isolation barrier adjacent to the nose and mouth there is an open access window 404 that allows the physician free access to the nose and/or mouth of the subject with, e.g., and instrument 405. The open access window is covered with a sealing flap 406 that is attached with a hinge 408 to the top of the cutout of the isolation barrier, just above the nose of the subject, proximal to, or in the vicinity of, the nasal bone allowing manipulation of the anterior portion of the nose. The sealing flap 406 is configured to form a seal when it is in the closed position shown in FIG. 17B, effectively closing and sealing off the open access window and preventing the release of particulates, pathogens and/or aerosols from the isolation barrier system. A snap or other attachment mechanism 407 may hold the flap in its closed position.

Although the flap can be affixed and hinged in a variety of ways that someone skilled in the art could imagine, in this embodiment, the flap is affixed using one or more tags that extends from the top of the flap that snap into small openings in the support structure of the isolation barrier creating hinge 408. The flap is made of a flexible rubber with a medium durometer (~50-70 shore A). The flap is transparent or translucent. To allow access to the subject's nose and/or mouth, the flap may be lifted up from the sealed position, pivoting on the top hinge, and held up in the open position by the user or by one or more instruments 405 being used in the procedure, to allow access to subject's nose and/or mouth. The flap 406 is configured by means of structure, spring, elastic deformation, magnetic elements, shape memory, and/or weight to return immediately to the closed and sealed position when released.

On the sides adjacent to the hinged edge there are accordion drapes 410 made of a thin flexible rubber, filter material, or other material, affixed to the flap and to the isolation barrier and configures so as to fold, in an accordion fashion, when the access flat is in the closed an sealed configuration. When the flap 406 is raised to allow access to the subject's nose and or mouth, the drapes 410 unfold and expand in such a manner as to affect a baffle or enclosure on the two sides of the isolation barrier adjacent to the open access window. The accordion type drapes are of sufficient flexibility so as not to inhibit the physician during instrument or tool manipulation.

The flap 406 can be rotated open to roughly 90 degrees or more, as measured from the closed and sealed position, to allow physician or healthcare worker access to the subject's nose or mouth. In some embodiments the flap may comprise one or more instrument access ports in the face of the transparent flap so as to provide tool access even in the closed position.

In one use scenario, the subject enters the exam room and affixes the isolation barrier 400 onto her face, wherein the isolation barrier is initially configured such that the flap is closed and the airflow outlet port is sealed with an air filter element. The healthcare worker then enters the room, removes the outlet air filter from the isolation barrier, attaches the airflow conduit to the airflow outlet port, connects the other end of the airflow conduit to the air mover and starts the isolation barrier system so as to create a desired airflow pattern and negative pressure field in and around the isolation barrier. The high volumetric airflow in the isolation barrier system begins replacing the air inside the isolation barrier with air from the room by means of the airflow input port, moving the subject's air from the isolation barrier into the air conduit by means of the airflow output port, through the airflow conduit to the filter, through the filter, cleaning the air, into the air mover, and releasing the clean air back into the room, preventing the unintentional release of respiratory exhalations and associated particulates, pathogens and/or aerosols from the subject.

The healthcare worker then starts the exam by lifting up on the access flap 406 (opening the access port), inserting the tip of a spray bottle into each nostril, spraying the inside of the nose and nasal cavity with anesthetic, removing the spray bottle, and allowing the flap close and seal. During the spraying process, the airflow within the isolation barrier is traveling at a volume flow rate and velocity that is greater than the respiratory exhalation rates from the subject in and around the nose and mouth, so as prevent unintended release of the subject's exhalation into the room.

While the healthcare worker allows the anesthetic to be absorbed and take effect, the air inside the isolation barrier is changing over constantly, ensuring the region in front of the subject's airway is clean of the subject exhalation particulates, pathogens and aerosols. Next the healthcare worker lifts the flap using a rigid endoscope and advances the scope into the isolation barrier. Using the other hand, the healthcare worker follows the scope with a procedure instrument into the isolation barrier and advances the instrument into a nasal cavity. The healthcare worker advances both instruments into the nasal cavity and performs the needed exam or procedure. The endoscope continues to hold the flap open and moves against the flap keeping the access window open.

If the subject feels the imminent occurrence of an episodic respiration event (such as a sneeze) about to happen during the procedure, the healthcare worker can rapidly remove the instruments from the nasal cavity and from the isolation barrier, allowing the flap to close and seal the isolation barrier. During the episodic respiration event, the flap acts as a barrier catching any aerosols, particulates, pathogens and ejecta that are not captured by the airflow. Once the event is over, the healthcare worker allows the air inside the isolation barrier to be exchanged for several minutes, opens the flap, and begins the procedure again.

FIGS. 18A-25 show how the placement of the inlet port or ports and the outlet port or ports can affect the airflow within the medical procedure field formed between an isolation barrier and a subject's face. In each of these embodiments, the outlet port or ports are connected to an air mover that evacuates air from the medical procedure field formed between the isolation barrier and the subject's face, and air enters the medical procedure field through an inlet. The inlet may be open to room air, or it may be connected to a return line from the air mover. There may be filters in one or both of the inlet and the outlet. Any of these arrangements may be employed with any of the embodiments described above.

Figure 18A:
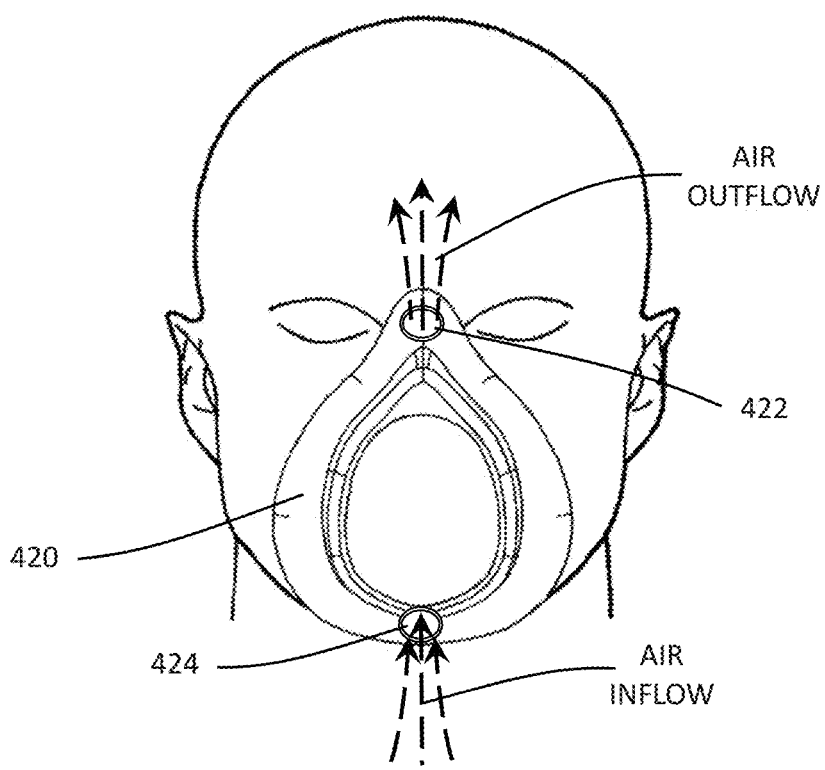
FIGS. 18A and 18B illustrate an isolation barrier according to an embodiment of this invention with a linear airflow pattern through the medical procedure field.
Figure 18B:
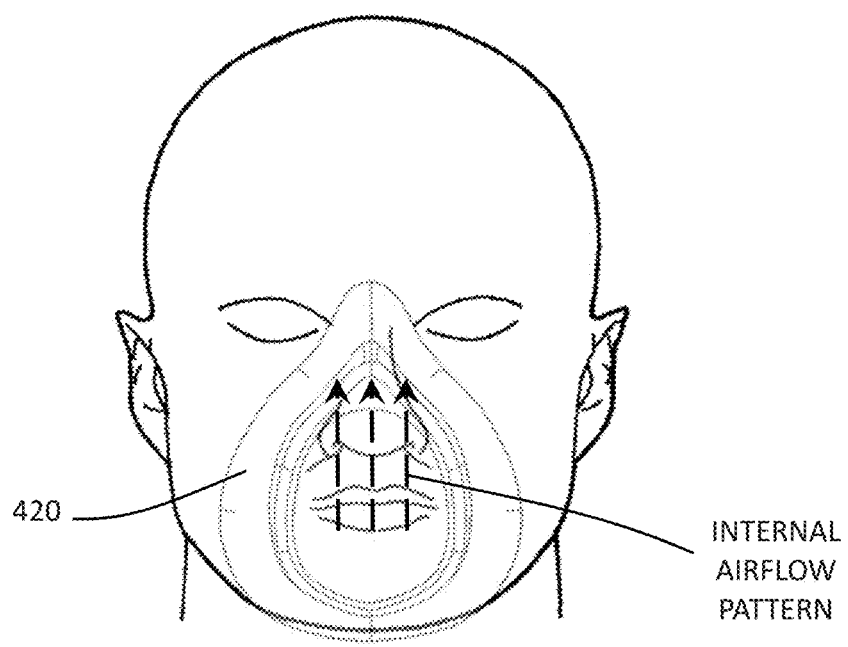

In FIGS. 18A-B, the outlet port 422 of isolation barrier 420 is at the top, and the inlet port 424 is at the bottom. This configuration provides a substantially linear air flow pattern within the medical procedure field between isolation barrier 420 and the subject's face, as shown in the transparent view of FIG. 18B.

Figure 19A:
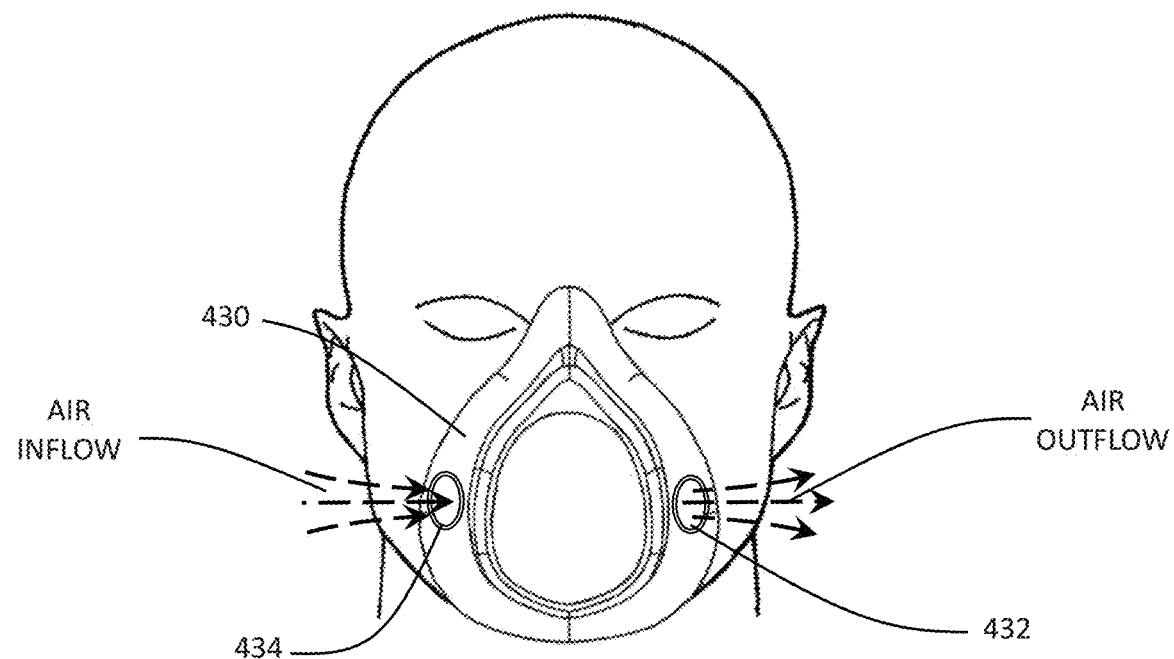
FIGS. 19A and 19B illustrate an isolation barrier according to another embodiment of this invention with a linear airflow pattern through the medical procedure field.
Figure 19B:
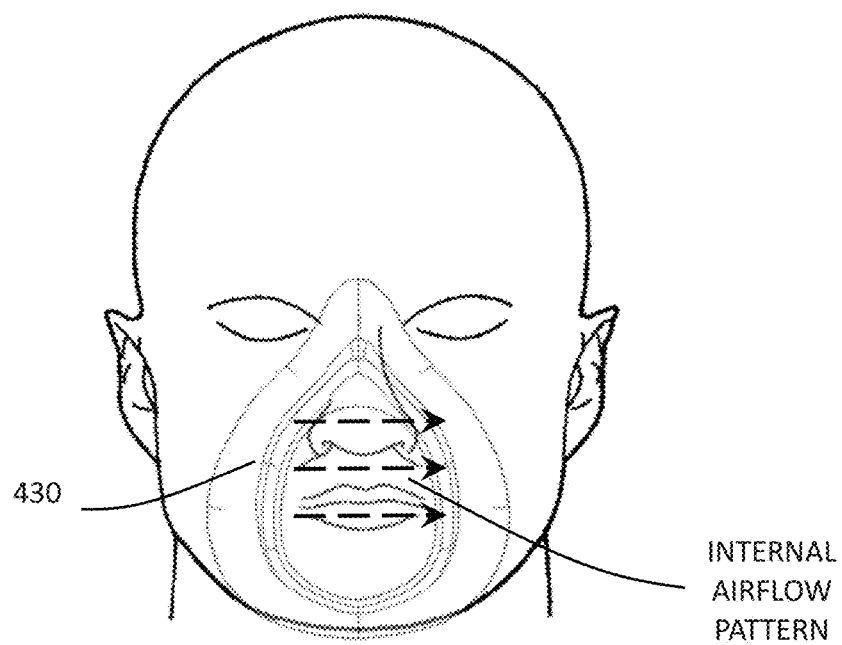

In FIGS. 19A-19B, the inlet port 434 and the outlet port 432 are on the sides of isolation barrier 430. This configuration provides a substantially linear air flow pattern within the medical procedure field between isolation barrier 430 and the subject's face, as shown in the transparent view of FIG. 19B.

Figure 20A:
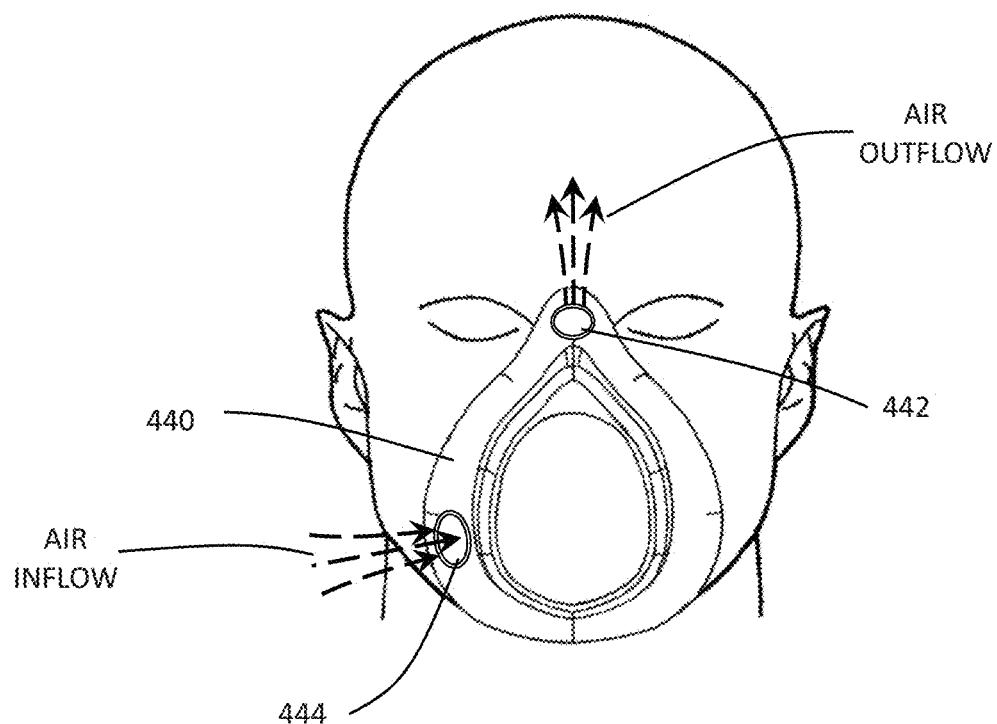
FIGS. 20A and 20B illustrate an isolation barrier according to an embodiment of this invention with a curved airflow pattern through the medical procedure field.
Figure 20B:
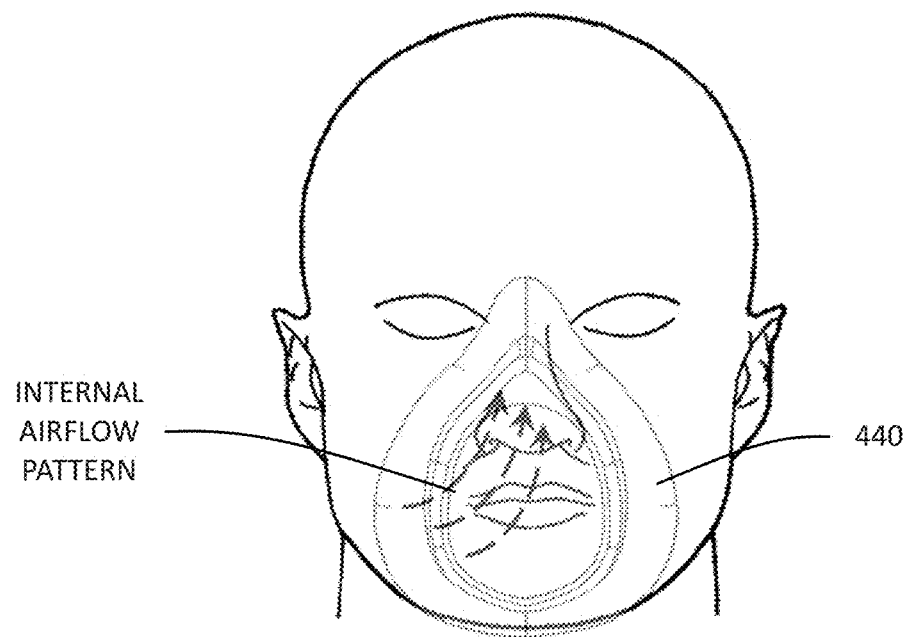

In FIGS. 20A-20B, the inlet port 444 is on the side of the isolation barrier 440, and the outlet port 442 is on the top. This configuration provides a substantially curved air flow pattern within the medical procedure field between isolation barrier 440 and the subject's face, as shown in the transparent view of FIG. 20B.

Figure 21A:
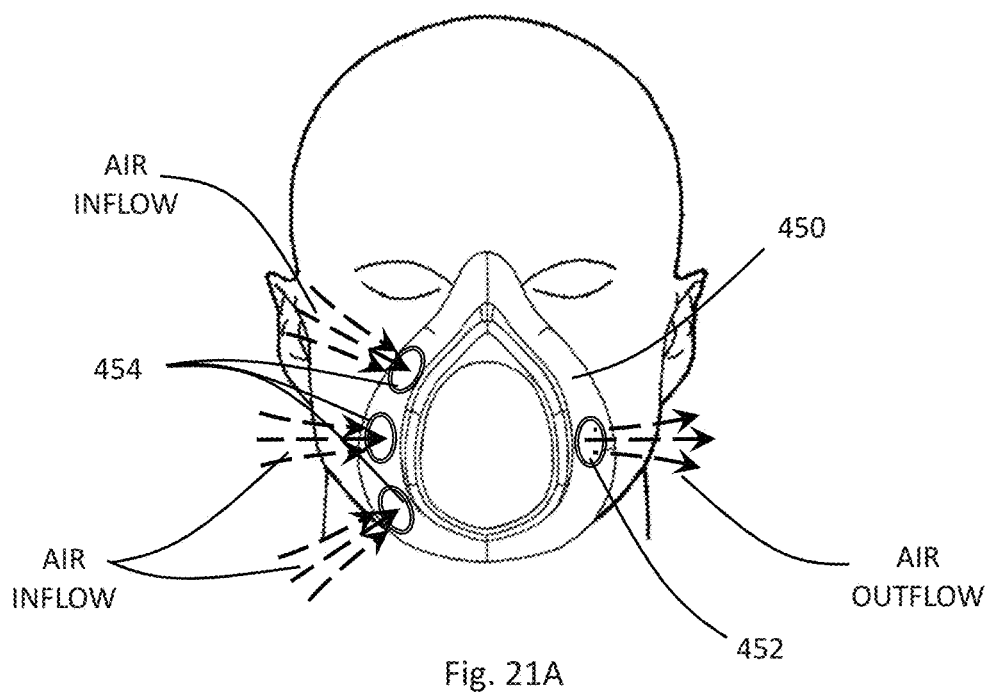
FIGS. 21A and 21B illustrate an isolation barrier according to an embodiment of this invention with a converging airflow pattern through the medical procedure field.
Figure 21B:
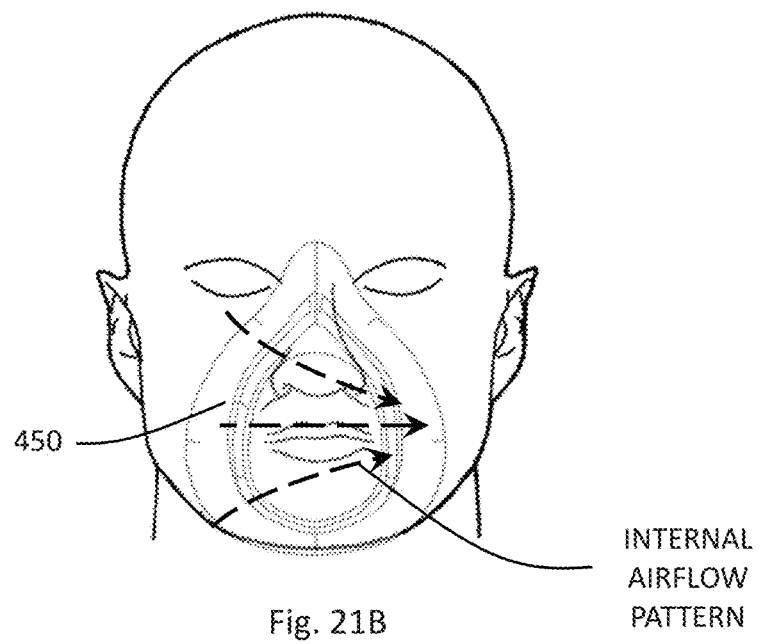

In FIGS. 21A-21B, there are multiple inlet ports 454 on one side of the isolation barrier 450 and one outlet port 452 on the other side. This configuration provides a substantially converging air flow pattern within the medical procedure field between isolation barrier 450 and the subject's face, as shown in the transparent view of FIG. 21B.

Figure 22A:
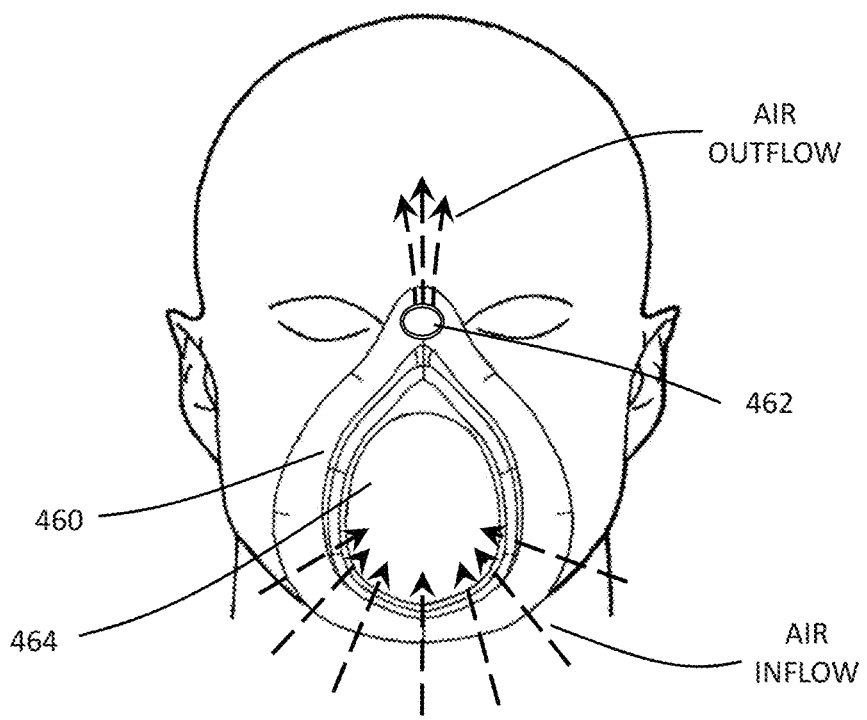
FIGS. 22A and 22B illustrate an isolation barrier according to another embodiment of this invention with a converging airflow pattern through the medical procedure field.
Figure 22B:
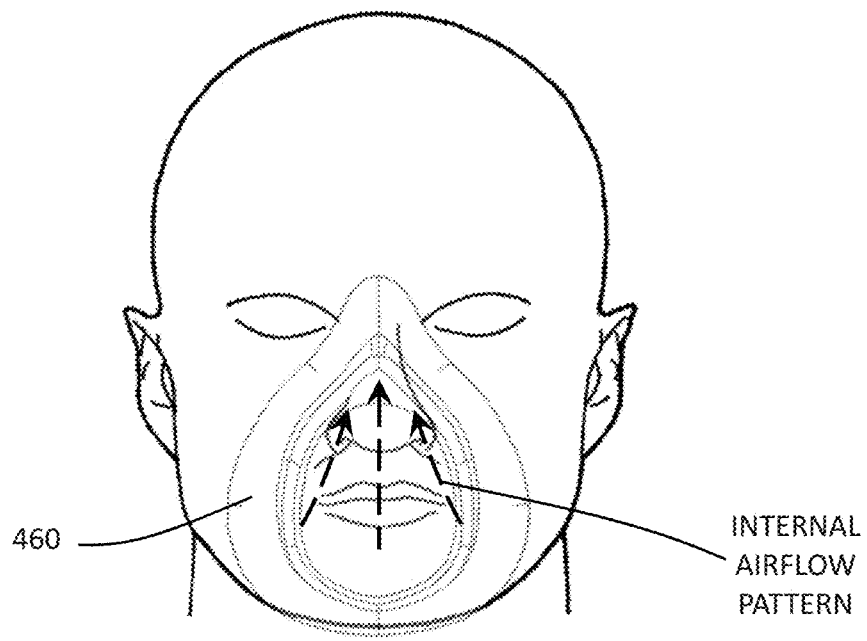

In FIGS. 22A-22B, there is a large inlet port 464 in the front of the isolation barrier 460 and one smaller outlet port 462 at the top. This configuration provides a substantially converging air flow pattern within the medical procedure field between isolation barrier 460 and the subject's face, as shown in the transparent view of FIG. 22B.

Figure 23A:
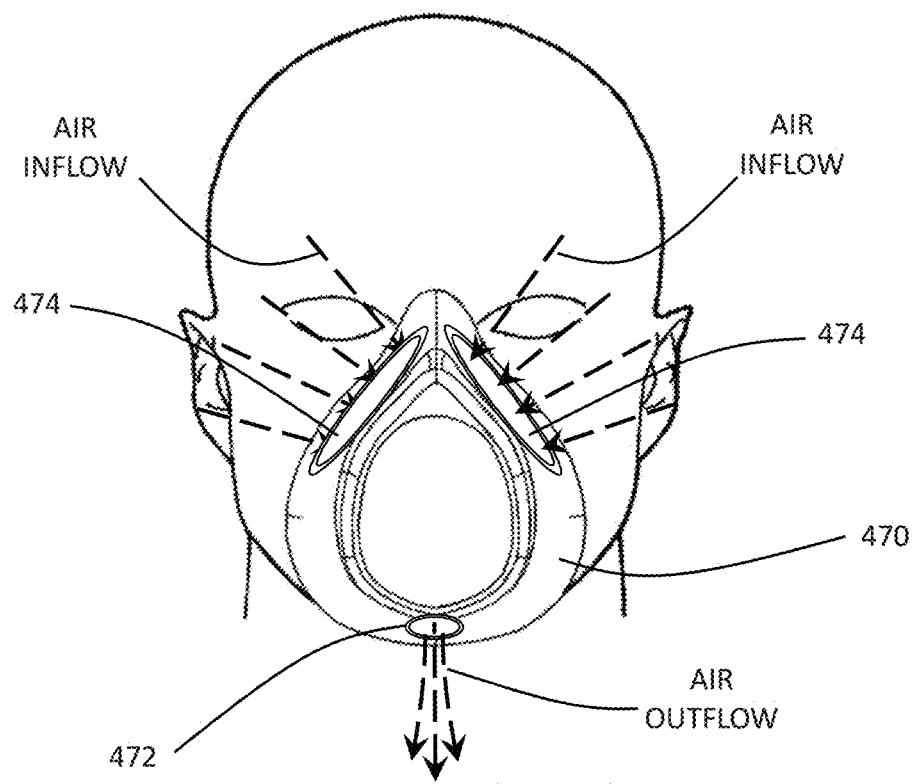
FIGS. 23A and 23B illustrate an isolation barrier according to yet another embodiment of this invention with a converging airflow pattern through the medical procedure field.
Figure 23B:
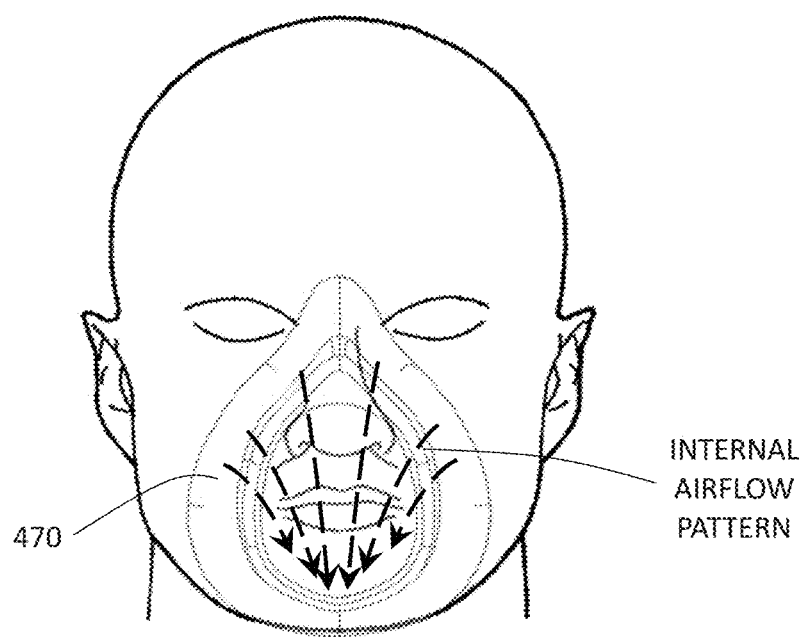

In FIGS. 23A-23B, there are two large inlet ports 474 at the top of isolation barrier 470 and one small outlet port 472 at the bottom. This configuration provides a substantially converging air flow pattern within the medical procedure field between isolation barrier 470 and the subject's face, as shown in the transparent view of FIG. 23B.

Figure 24A:
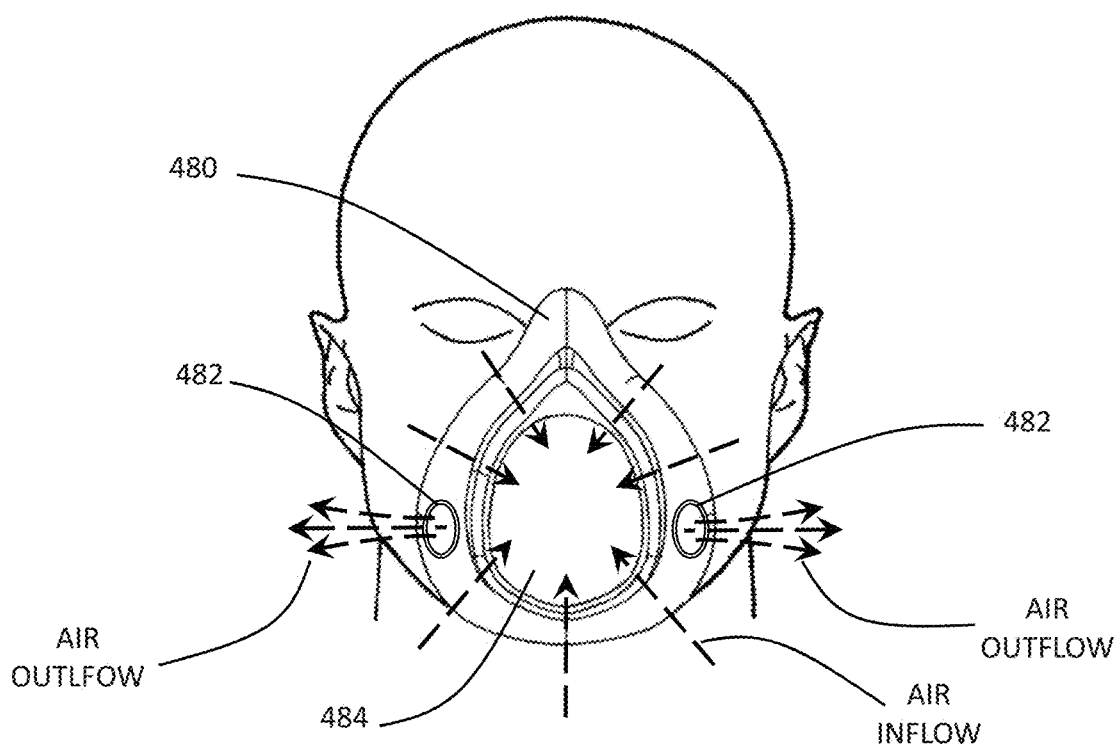
FIGS. 24A and 24B illustrate an isolation barrier according to an embodiment of this invention with a diverging airflow pattern through the medical procedure field.
Figure 24B:
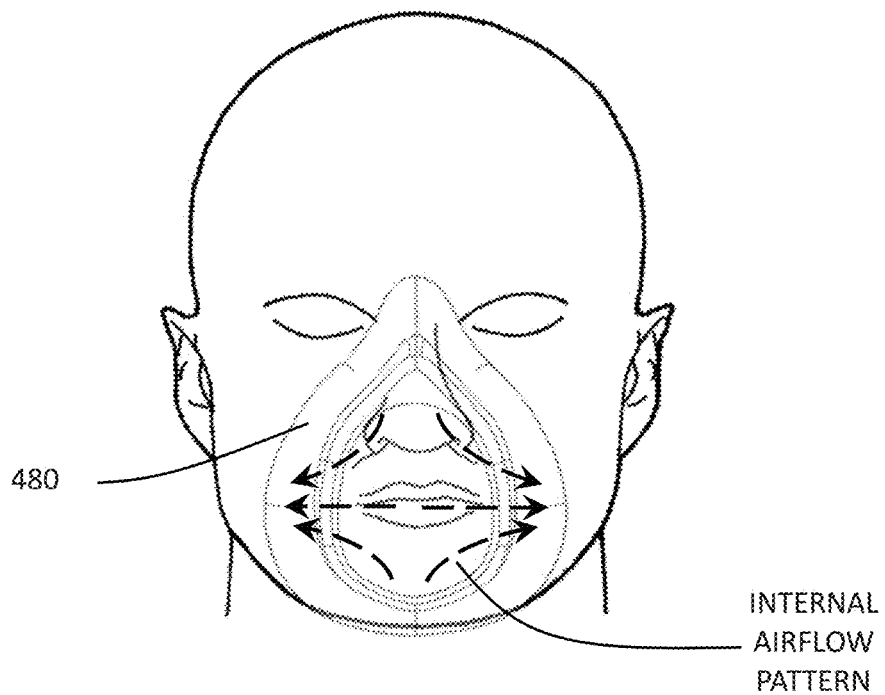

In FIGS. 24A-24B, there is a large inlet port 484 in the front of the isolation barrier 480 and two smaller outlet ports 482 at the sides. This configuration provides a substantially converging air flow pattern within the medical procedure field between isolation barrier 480 and the subject's face, as shown in the transparent view of FIG. 24B.

In FIG. 25, there are multiple inlet ports 494 on one side of the isolation barrier 490 and one larger outlet port 492 on the other side. An access panel may be opened to access the medical procedure field. This configuration provides a substantially laminar flow within the medical procedure field between isolation barrier 490 and the subject's face.

Figure 26:
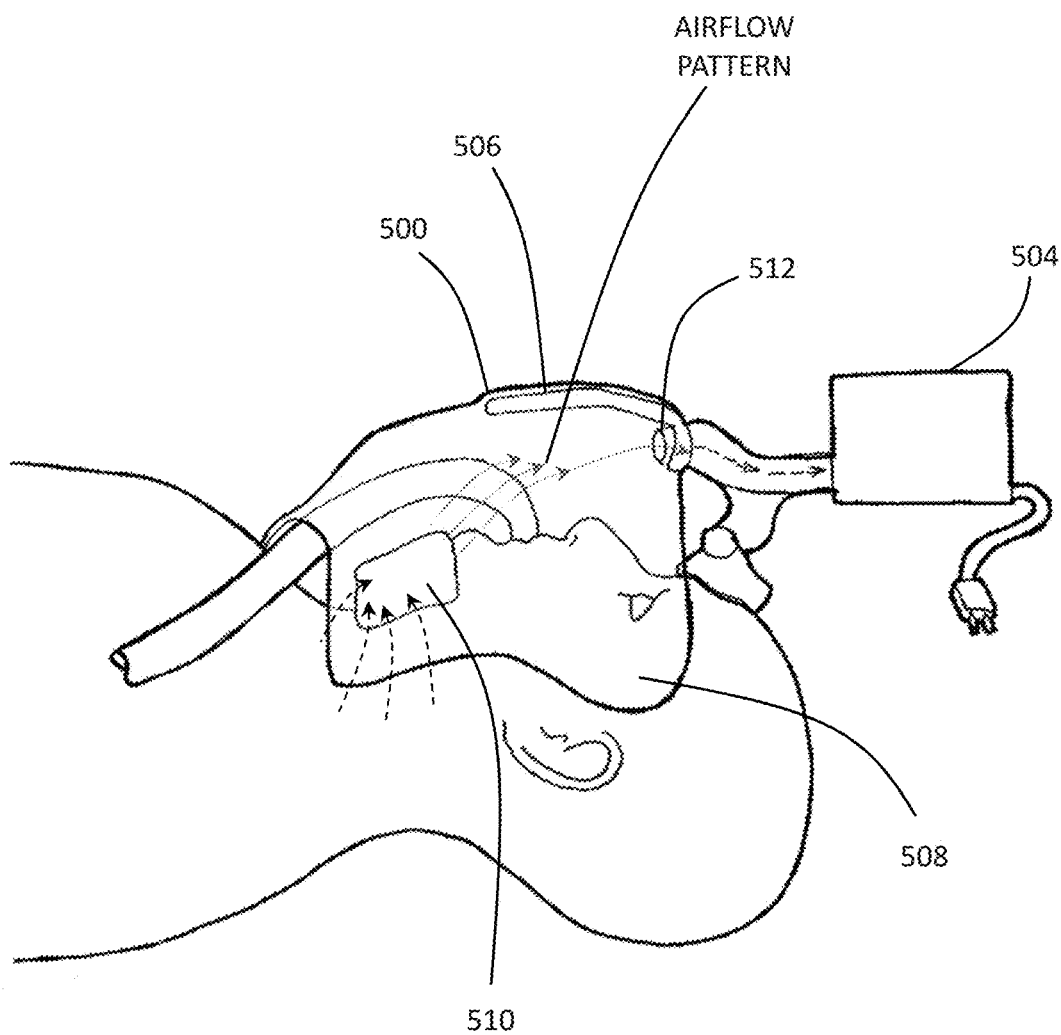
FIG. 26 is a side elevational view of a system for creating an isolated medical procedure field around a subject's nose and mouth according to still another embodiment of the invention, in place on a subject to create the medical procedure field.

In the embodiment of FIG. 26, the isolation barrier system includes an isolation barrier 500, an air conduit 502, a filter (not shown), and an air mover 504. A support structure 506 supports a transparent or translucent drape 508 that, together with the subject's face, at least partially define a medical procedure field 509. An air inlet port 510 in the drape leads to the medical procedure field 509, and an outlet port 512 lads to air conduit 502. Air mover 504 draws air from the medical procedure field 509 through outlet port 512 and conduit 502 to maintain a negative pressure in the medical procedure field. The support structure is comprised of malleable plastic or metal rods, tubes, bars, or any other material or shape, and may be formed from a plurality of small segmented rigid or semi-rigid components affixed together in a manner so as to allow safely and effectively support elements of the isolation barrier system. The transparent drape is comprised of one or more thin film polymer elements constructed from material such as urethane, polyethylene, PVC, or any other suitable material, one or more weights, attachments, and/or clips to keep the transparent drape in the desired configuration during use. The drape is configured to provide a physical barrier that covers at least the mouth and nose of a subject and in this embodiment covers the entire front and sides of the subject's head. The drape is affixed to the support structure. The support structure creates a raised scaffolding around the subject's face and head, and attaches to the subject's forehead and/or rests on the bed or surgical drapes around the subject's head. The transparent drape may be sized to cover the support structure and hang down over the subject's head and rest on the surgical bed or chair. The weight of the drape or elements within the drape keep the drape in place affecting the isolation barrier in such a manner as to prevent the subject's respiratory exhalations and associated particulates, pathogens and/or aerosols from exiting the barrier. The air inlet and outlet ports are affixed or built into the drape or support structure. In this embodiment, the air inlet(s) are sewn in filtered ports positioned around the face and the air outlet is positioned above the subject's between the hairline and the tip of the nose to be out of the way of the procedural instrumentation field and potential air breathing tubes.

In one use scenario, the isolation barrier 500 is placed over the subject's head to form a structure similar to a tent. The support structure is configured to create an instrumentation access space within the isolation barrier, having a vertical height of at least 100 mm above the nasal sill and of sufficient horizontal dimensions to enable the surgical procedure and associated tools and instruments. The drape lays over and/or affixes to the support structure and rest against the surgical drapes placed over the subject and the surgical bed by means of weights and/or clips. The healthcare worker then attaches the airflow conduit (that is attached to the filter that is in turn attached to the air mover) to the air outlet port and turns on the air mover. The high volume airflow begins replacing air from inside the isolation barrier with air from the room, moving the air within the isolation barrier into the air conduit, through the filter, into the air mover, filtering the air and releasing it back into the room.

Once the isolation barrier system is setup, the healthcare worker reaches her gloved hands under the drape of the isolation barrier and anesthetizes the subject and intubating the subject. Once the subject is asleep, the healthcare provider begins the procedure by placing her hands under the drapes, accessing the desired airway cavity while viewing her work through the drape. During this surgical procedure, the aerosolization caused by the manipulation of the airway tissue is be evacuated from the isolation barrier through the air outlet conduit and filtered before allowing the air to release back into the room. After the procedure is complete, the isolation barrier system is allowed to run for several minutes, allowing the air in the isolation barrier to change multiple times. The healthcare worker then wakes up the subject, removes the breathing tube within the isolation barrier while viewing through the transparent drape and places a mask on the subject. The healthcare worked then removes her hands and allows the air to change within the isolation barrier for a few more minutes. After that the isolation barrier detached from the air conduit, the isolation barrier is discarded and the subject is transferred to the recovery room.

Figure 27:
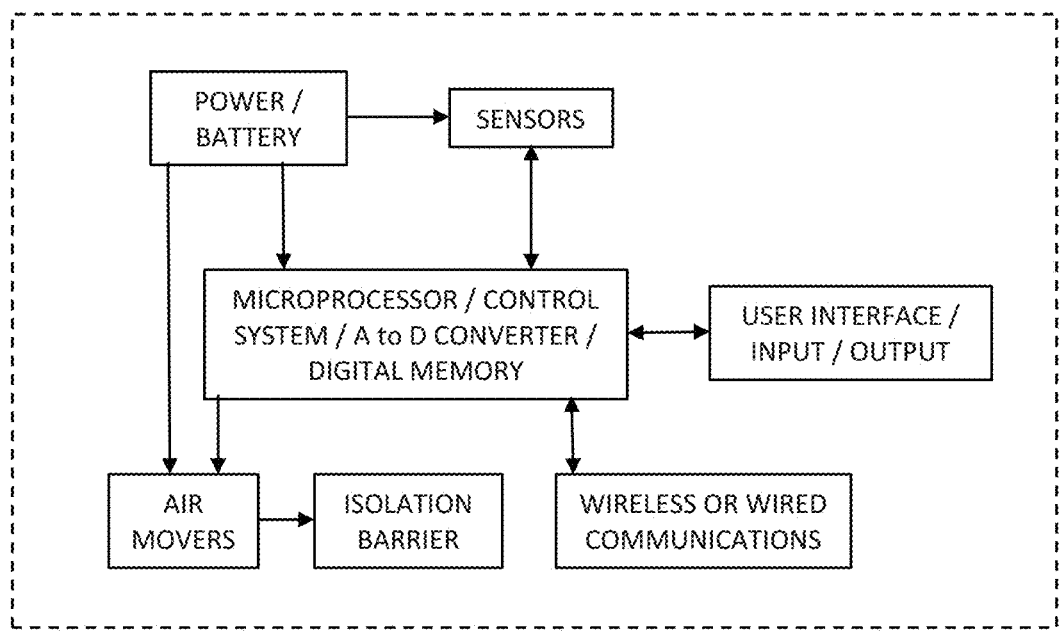
FIG. 27 is a block diagram showing aspects of a system for creating an isolated medical procedure field.

FIG. 27 is a block diagram illustrating the components of the isolation barrier systems of this invention.

In the embodiments described herein, the air mover removes air from the medical procedure field at a rate equal to or greater than the subject's respiratory minute volume (e.g., at an air evacuation rate greater than or equal to 10 liters/minute). In some embodiments, the removal rate of air from the medical procedure field creates a negative pressure in that field (e.g., a negative pressure of 0.14-68 cm $H_2O$). After the isolation barrier is placed on a subject to form the medical procedure field, healthcare providers can perform medical procedures in, through, or on the subject's oral and nasal cavities via the medical procedure field without being exposed to aerosols or other ejecta from the patient's breath.

The foregoing methods and techniques can be similarly implemented in conjunction with other medical and surgical procedures in files such as dental, periodontal, orthodontal, sinus, nasal, laryngeal, and any other nose, mouth, throat, or upper gastro-intestinal medicine, where the healthcare professionals work in or around an upper airway cavity of a patient and may need to ensure that particles, pathogens, and/or aerosols from the patient are controlled and isolated during the medical procedure.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of performing a procedure in or around a subject's nose or mouth, the method comprising:
   evacuating air from a medical procedure field adjacent to the subject's nose and mouth at an air evacuation rate greater than or equal to the subject's respiratory minute volume, the medical procedure field being bordered at least partially by a face of the subject and an isolation barrier disposed against the face of the subject, the isolation barrier controlling air flow into the medical procedure field, the isolation barrier comprising an expandable portion adapted to accommodate a sudden increase in volume or momentum of an exhalation of the subject;
   expanding the expandable portion to accommodate a cough or a sneeze of the subject; and
   accessing the subject's nose or mouth within the medical procedure field through an opening in the expandable portion of the isolation barrier to perform the procedure.

2. The method of claim 1 wherein the air evacuation rate is greater than or equal to 10 liters/minute.

3. The method of claim 1 further comprising maintaining a negative pressure within the medical procedure field.

4. The method of claim 3 wherein the negative pressure is 0.14-68 cm $H_2O$.

5. The method of claim 3 further comprising maintaining the negative pressure within the medical procedure field when the subject coughs or sneezes.

6. The method of claim 1 wherein the isolation barrier comprises a transparent portion through which the medical procedure field can be viewed, the method further comprising viewing the subject's nose or mouth through the transparent portion of the isolation barrier.

7. The method of claim 1 further comprising filtering air evacuated from the medical procedure field.

8. The method of claim 1 wherein the accessing step comprises inserting an instrument through a port in the isolation barrier.

9. The method of claim 8 wherein the inserting step comprises inserting the instrument through a seal of the port.

10. The method of claim 1 further comprising deflating the expandable portion after the expanding step.

11. The method of claim 1 wherein the isolation barrier further comprises a face component adapted to engage the subject's face and to at least partially surround the subject's nose and mouth, the method further comprising detaching the expandable portion from the face component after the accessing step.

12. A method of performing a procedure in or around a subject's nose or mouth, the method comprising:
   evacuating air from within an isolation barrier at least partially defining a medical procedure field adjacent to the subject's nose and mouth at an air evacuation rate greater than or equal to the subject's respiratory minute volume, the isolation barrier being engaged with the subject's face surrounding the subject's nose and mouth, the isolation barrier comprising an expandable portion adapted to accommodate a sudden increase in volume or momentum of an exhalation of the subject;

expanding the expandable portion to accommodate a cough or a sneeze of the subject; and accessing the subject's nose or mouth within the medical procedure field through an opening in the expandable portion of the isolation barrier to perform the procedure.

13. The method of claim 12 wherein the air evacuation rate is greater than or equal to 10 liters/minute.

14. The method of claim 12 further comprising maintaining a negative pressure within the medical procedure field.

15. The method of claim 14 wherein the negative pressure is 0.14-68 cm $H_2O$.

16. The method of claim 14 further comprising maintaining a negative pressure within the medical procedure field when the subject coughs or sneezes.

17. The method of claim 12 wherein the isolation barrier comprises a transparent portion through which the medical procedure field can be viewed, the method further comprising viewing the subject's nose or mouth through the transparent portion of the isolation barrier.

18. The method of claim 12 further comprising filtering air evacuated from the medical procedure field.

19. The method of claim 12 wherein the accessing step comprises inserting an instrument through a port in the isolation barrier.

20. The method of claim 19 wherein the inserting step comprises inserting the instrument through a seal of the port.

21. The method of claim 12 further comprising deflating the expandable portion after the expanding step.

22. The method of claim 12 wherein the isolation barrier further comprises a face component adapted to engage the subject's face and to at least partially surround the subject's nose and mouth, the method further comprising detaching the expandable portion from the face component after the accessing step.

23. A method of performing a procedure in or around a subject's nose or mouth, the method comprising:

evacuating air from a medical procedure field adjacent to the subject's nose and mouth to create a negative pressure within the medical procedure field, the medical procedure field being bordered at least partially by a face of the subject and an isolation barrier disposed against the face of the subject, the isolation barrier controlling air flow into the medical procedure field;

expanding an expandable portion of the isolation barrier to accommodate a cough or a sneeze of the subject; and accessing the subject's nose or mouth within the medical procedure field through an opening in the expandable portion to perform the procedure.

24. The method of claim 23 wherein the negative pressure is 0.14-68 cm $H_2O$.

25. The method of claim 23 further comprising maintaining the negative pressure within the medical procedure field when the subject coughs or sneezes.

26. The method of claim 23 wherein the isolation barrier comprises a transparent portion through which the medical procedure field can be viewed, the method further comprising viewing the subject's nose or mouth through the transparent portion of the isolation barrier.

27. A method of performing a procedure in or around a subject's nose or mouth, the method comprising:

evacuating air from within an isolation barrier at least partially defining a medical procedure field adjacent to the subject's nose and mouth to create a negative pressure within the medical procedure field, the isolation barrier being engaged with the subject's face surrounding the subject's nose and mouth;

expanding an expandable portion of the isolation barrier to accommodate a cough or a sneeze of the subject; and accessing the subject's nose or mouth within the medical procedure field through an opening in the expandable portion to perform the procedure.

28. The method of claim 27 wherein the negative pressure is 0.14-68 cm $H_2O$.

29. The method of claim 27 further comprising maintaining the negative pressure within the medical procedure field when the subject coughs or sneezes.

30. The method of claim 27 wherein the isolation barrier comprises a transparent portion through which the medical procedure field can be viewed, the method further comprising viewing the subject's nose or mouth through the transparent portion of the isolation barrier.

31. A method of performing a procedure in or around a subject's nose or mouth, the method comprising:

evacuating air from within an isolation barrier at least partially defining a medical procedure field adjacent to the subject's nose and mouth to create a negative pressure within the medical procedure field, the isolation barrier comprising an expandable portion adapted to accommodate a sudden increase in volume or momentum of an exhalation of the subject and a face component adapted to engage the subject's face and to at least partially surround the subject's nose and mouth, the isolation barrier controlling air flow into the medical procedure field;

accessing the subject's nose or mouth within the medical procedure field through the expandable portion to perform the procedure; and detaching the expandable portion from the face component after the accessing step.

32. The method of claim 31 wherein the negative pressure is 0.14-68 cm $H_2O$.

33. The method of claim 31 further comprising maintaining the negative pressure within the medical procedure field when the subject coughs or sneezes.

34. The method of claim 31 wherein the isolation barrier comprises a transparent portion through which the medical procedure field can be viewed, the method further comprising viewing the subject's nose or mouth through the transparent portion of the isolation barrier.

35. A method of performing a procedure in or around a subject's nose or mouth, the method comprising:

evacuating air from within an isolation barrier at least partially defining a medical procedure field adjacent to the subject's nose and mouth to create a negative pressure within the medical procedure field, the isolation barrier comprising an expandable portion adapted to accommodate a sudden increase in volume or momentum of an exhalation of the subject and a face component adapted to engage the subject's face and to at least partially surround the subject's nose and mouth;

accessing the subject's nose or mouth within the medical procedure field through the expandable portion to perform the procedure; and detaching the expandable portion from the face component after the accessing step.

36. The method of claim 35 wherein the negative pressure is 0.14-68 cm $H_2O$.

37. The method of claim 35 further comprising maintaining the negative pressure within the medical procedure field when the subject coughs or sneezes.

38. The method of claim 35 wherein the isolation barrier comprises a transparent portion through which the medical procedure field can be viewed, the method further comprising viewing the subject's nose or mouth through the transparent portion of the isolation barrier.

* * * * *